(12) United States Patent
Talbot et al.

(10) Patent No.: US 8,512,276 B2
(45) Date of Patent: Aug. 20, 2013

(54) SYSTEM FOR PROVIDING BLOOD GLUCOSE MEASUREMENTS TO AN INFUSION DEVICE

(75) Inventors: Cary D. Talbot, Santa Clarita, CA (US); Mark C. Estes, Simi Valley, CA (US); John J. Mastrototaro, Los Angeles, CA (US); Sheldon B. Moberg, Thousand Oaks, CA (US); John C. Mueller, Jr., Simi Valley, CA (US); "Mike" Charles Vallet Tolle, Van Nuys, CA (US); Gary L. Williams, Gardena, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 2585 days.

(21) Appl. No.: 10/867,529

(22) Filed: Jun. 14, 2004

(65) Prior Publication Data

US 2005/0065464 A1    Mar. 24, 2005

Related U.S. Application Data

(63) Continuation-in-part of application No. 10/624,389, filed on Jul. 22, 2003, now abandoned.

(60) Provisional application No. 60/478,697, filed on Jun. 13, 2003, provisional application No. 60/398,199, filed on Jul. 24, 2002, provisional application No. 60/412,998, filed on Sep. 23, 2002.

(51) Int. Cl.
*A61M 5/30*    (2006.01)

(52) U.S. Cl.
USPC .......................................................... 604/65

(58) Field of Classification Search
USPC .............. 604/65–67, 890.1, 891.1; 600/365, 600/300, 309
See application file for complete search history.

(56) References Cited

U.S. PATENT DOCUMENTS

| | | |
|---|---|---|
| 4,433,072 A | 2/1984 | Pusineri et al. |
| 4,494,950 A | 1/1985 | Fischell |
| 4,562,751 A | 1/1986 | Nason et al. |

(Continued)

FOREIGN PATENT DOCUMENTS

| | | |
|---|---|---|
| EP | 1338295 | 8/2003 |
| EP | 1338295 A1 | 8/2003 |
| WO | WO 96/37246 A1 | 11/1996 |
| WO | WO 02/058537 A2 | 8/2002 |

OTHER PUBLICATIONS

PCT: International Search Report for Application No. PCT/US2007/024441 (dated Apr. 1, 2008; 4 pgs.).

(Continued)

*Primary Examiner* — Nicholas D Lucchesi
*Assistant Examiner* — Pritesh Patel
(74) *Attorney, Agent, or Firm* — Pillsbury Winthrop Shaw Pittman LLP

(57) ABSTRACT

An infusion system includes an infusion device and a sensing device. The infusion system may further include a characteristic determining device. The infusion device also includes a communication system for transmitting to and receiving communications from the sensing device or a computer. The sensing device may sense an analyte of a bodily fluid of the user. The analyte may be calibrated using data from the infusion device and from a characteristic determining device. The system may be set up to automatically call for assistance when analytes reach a certain level.

25 Claims, 8 Drawing Sheets

(56) References Cited

U.S. PATENT DOCUMENTS

| | | |
|---|---|---|
| 4,671,288 A | 6/1987 | Gough |
| 4,678,408 A | 7/1987 | Nason et al. |
| 4,685,903 A | 8/1987 | Cable et al. |
| 4,731,726 A | 3/1988 | Allen, III |
| 4,781,798 A | 11/1988 | Gough |
| 4,871,351 A | 10/1989 | Feingold |
| 5,080,653 A | 1/1992 | Voss et al. |
| 5,097,122 A | 3/1992 | Colman et al. |
| 5,101,814 A | 4/1992 | Palti |
| 5,108,819 A | 4/1992 | Heller et al. |
| 5,165,407 A | 11/1992 | Wilson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,320,725 A | 6/1994 | Gregg et al. |
| 5,322,063 A | 6/1994 | Allen et al. |
| 5,356,786 A | 10/1994 | Heller et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,497,772 A | 3/1996 | Schulman et al. |
| 5,543,326 A | 8/1996 | Heller et al. |
| 5,569,186 A | 10/1996 | Lord et al. |
| 5,586,553 A | 12/1996 | Halili et al. |
| 5,593,852 A | 1/1997 | Heller et al. |
| 5,660,163 A | 8/1997 | Schulman et al. |
| 5,665,065 A | 9/1997 | Colman et al. |
| 5,665,222 A | 9/1997 | Heller et al. |
| 5,750,926 A | 5/1998 | Schulman et al. |
| 5,779,665 A | 7/1998 | Mastrototaro et al. |
| 5,791,344 A | 8/1998 | Schulman et al. |
| 5,904,708 A | 5/1999 | Goedeke |
| 5,917,346 A | 6/1999 | Gord et al. |
| 5,965,380 A | 10/1999 | Heller et al. |
| 5,972,199 A | 10/1999 | Heller et al. |
| 5,999,848 A | 12/1999 | Gord et al. |
| 5,999,849 A | 12/1999 | Gord et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,259,937 B1 | 7/2001 | Schulman et al. |
| 6,329,161 B1 | 12/2001 | Heller et al. |
| 6,472,122 B1 | 10/2002 | Schulman et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,554,798 B1 | 4/2003 | Mann et al. |
| 6,558,320 B1 | 5/2003 | Causey, III et al. |
| 6,560,471 B1 | 5/2003 | Heller et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,733,471 B1 | 5/2004 | Ericson et al. |
| 6,746,582 B2 | 6/2004 | Heller et al. |
| 6,749,740 B2 | 6/2004 | Liamos et al. |
| 6,809,653 B1 | 10/2004 | Mann et al. |
| 6,881,551 B2 | 4/2005 | Heller et al. |
| 6,893,545 B2 | 5/2005 | Gotoh et al. |
| 6,916,159 B2 | 7/2005 | Rush et al. |
| 6,932,894 B2 | 8/2005 | Mao et al. |
| 6,942,518 B2 | 9/2005 | Liamos et al. |
| 7,860,544 B2 * | 12/2010 | Say et al. ............... 600/347 |
| 2002/0082665 A1 | 6/2002 | Haller et al. |
| 2002/0161288 A1 | 10/2002 | Shin et al. |
| 2002/0165436 A1 | 11/2002 | Schluter et al. |
| 2003/0078560 A1 | 4/2003 | Miller et al. |
| 2003/0088166 A1 | 5/2003 | Say et al. |
| 2003/0152823 A1 | 8/2003 | Heller et al. |
| 2003/0168338 A1 | 8/2003 | Liamos et al. |
| 2003/0172940 A1 | 9/2003 | Rogers et al. |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0074785 A1 | 4/2004 | Holker et al. |
| 2004/0093167 A1 | 5/2004 | Braig et al. |
| 2004/0111017 A1 | 6/2004 | Say et al. |
| 2005/0182306 A1 * | 8/2005 | Sloan ............... 600/300 |
| 2005/0192557 A1 | 9/2005 | Brauker et al. |
| 2005/0214585 A1 | 9/2005 | Bernatz et al. |
| 2006/0025663 A1 * | 2/2006 | Talbot et al. ............. 600/365 |

OTHER PUBLICATIONS

Fernandez-Luque, J.L. Sevillano, F.J. Hurtado-Nunez, F.J. Moriana-Garcia, F. Diaz Del Rio, and D. Cascado: eDiab: A System for Monitoring, Assisting and Educating People with Diabetes; (ICCHP 2006, LNCS 4061, pp. 1342-1349).

International Preliminary Report on Patentability, (PCT/US2007/024441) (13-pgs).

International Search Report, pp. 4.

Reach et al., "Experience with an implantable glucose sensor as a prerequisite of an artificial beta cell," Biomed. Biochim. Acta, 1984, pp. 577-584, vol. 5.

Abel et al., "A Method for Evaluating in vivo the Functional Characteristics of Glucose Sensors," Biosensors, 1986, pp. 211-220, vol. 2.

Boguslavsky et al., "Applications of redox polymers in biosensors," Solid State Ionics, 1993, pp. 189-197, vol. 60.

Geise et al., "Electropolymerized 1,3-diaminobenzene for the construction of a 1-1'-dimethylferrocene mediated glucose biosensor," Analytica Chim. Acta.,1993, pp. 467-473, v18.

Gernet et al., "A planar glucose enzyme electrode," Sensors and Actuators, 1989, pp. 537-540, vol. 17, Elsevier Sequoia, Netherlands.

Gernet et al., "Fabrication and Characterization of a Planar Electrochemical Cell and Its Applications as a Glucose Sensor," Sensors and Actuators, 1989, pp. 49-70, vol. 18.

Gorton et al., "Amperometric glucose senosrs based on immobilized glucose-oxidizing enzymes and chemically modified electrodes," Analytica Chim Acta., 1991, pp. 43-54, v. 249.

Gorton et al., "Amperometric biosensors based on an apparent direct electron transfer between electrodes and immobilized peroxidases," Analyst, 1992, pp. 1235-1241, vol. 117.

Gough et al., "Two-Dimensional Enzyme Electrode Sensor for Glucose," Analytical Chemistry, 1985, pp. 2351-2357, vol. 57.

Gregg et al., "Redox polymer films containing enzymes," J. Phys. Chem., 1991, pp. 5970-5975.

Gregg et al., "Cross-Linked Redox Gels Containing Glucose Oxidase for Amperometric Biosensor Applications," Anal. Chem., 1990, pp. 258-263, vol. 62.

Heller et al., "Electrical Wiring of Redox Enzymes," Accounts of Chemical Research, 1990, pp. 128-134, vol. 23, No. 5.

Johnson et al., "In vivo evaluation of an electroenzymatic glucose sensor implanted in subcutaneous tissue," Biosensors & Bioelectronics, 1992, pp. 709-714, vol. 7.

Jonsson et al., "An Electrochemical Sensor for Hydrogen Peroxide Based on Peroxidase Adsorbed on a Spectrographic Graphite Electrode," Electroanalysts, 1989, pp. 465-468, v.1.

Kanapieniene et al., "Miniature glucose biosensor with extended linearity," Sensors and Actuators, 1992, pp. 37-40, vol. B, No. 10.

Kawamori et al., "Perfect Normalization of Excessive Glucagon Responses to Intravenous Arginine in Human Diabetes Mellitus With . . . ," Diabetes, 1980, pp. 762-765, vol. 29.

Kimura et al., "An immobilized Enzyme Membrane Fabrication Method using an Ink Jet Nozzle," Biosensors, 1988, pp. 41-52, vol. 4.

Koudelka et al., "In-vivio Behaviour of Hypodermically Implanted Microfabricated Glucose Sensors," Biosensors & Bioelectronics, 1991, pp. 31-36, vol. 6.

Mastrototaro et al., "An electroenzymatic glucbse sensor fabricated on a flexible substrate," Sensors and Actuators, 1991, pp. 139-144, vol. 5.

Mastrototaro et al., "An Electroenzymatic Sensor Capable of 72 Hour Continuous Monitoring of Subcutaneous Glucose," 14th Int'l Diabetes Federation Congress, 1991.

McKean et al., "A Telemetry-Instrumentation System for Chronically Implanted Glucose and Oxygen Sensors," IEEE Transactions on Biomedical Eng., 1988, pp. 526-532, vol. 35, No. 7.

Monroe, "Novel implantable glucose sensors," ACL, 1989, pp. 8-16.

Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n.2.

Nakamado et al., "A Lift-Off Method for Patterning Enzyme-Immobilized Membranes in Multi-Biosensors," Sensors and Actuators, 1988, pp. 165-172, vol. 13.

Nishida et al., "Clinical applications of the wearable artificial endocrine pancreas with the newly designed . . . ," Path. and Treat. of NIDDM . . . , 1994, p. 353-358, No. 1057.

Shichiri et al., "An artificial endocrine pancrease—problems awaiting solutions for long term clinical applications of . . . ," Frontiers Med. Biol. Eng., 1991, pp. 283-292, v.3.

Shichiri et al., "Wearable Artificial Endocrine Pancreas with Needle-Type Glucose Sensor," The Lancet, 1982, pp. 1129-1131, vol. 2 (8308).

Shichiri et al., "Telemetry Glucose Monitoring Device with Needle-Type Glucose Sensor," Diabetes Care, May-Jun. 1986, pp. 298-301, vol. 9, No. 3.

Shichiri et al., "Normalization of the Paradoxic Secretion of Glucagen in Diabetics Who Were Controlled by the Artificial Beta Cell," Diabetes, 1979, pp. 272-275, vol. 28.

Shichiri et al., "Closed-Loop Glycemic Control with a Wearable Artificial Endocrine Pancreas," Diabetes, 1984, pp. 1200-1202, vol. 33.

Shichiri et al., "In Vivo Characteristics of Needle-Type Glucose Sensor," Hormone and Metabolic Research, 1988, pp. 17-20, vol. 20.

Shichiri et al., "A Needle-Type Glucose Sensor," Life Support Systems: The Journal of the European Society for Artificial Organs, 1984, pp. 7-9, vol. 2, supplement 1.

Shichiri et al., "The Wearable Artificial Endocrine Pancreas with a Needle-Type Glucose Sensor," Acta Pediatr, Jpn, 1984, pp. 358-370, vol. 26.

Shichiri et al., "Glycaemic Control in Pancreatectomized Dogs with a Wearable Artificial Endocrine Pancreas," Diabetblogica, 1983, pp. 179-184, vol. 24.

Shichiri et al., "Membrane design for extending the long-life of an implantable glucose sensor," Diab. Nutr. Metab., 1989, pp. 309-313, vol. 2.

Shinkai et al., "Molecular Recognition of Mono- and Di-Saccharides by Phenylboronic Acids in Solvent Extraction and as a Monolayer," J. Chem. Soc., 1991, pp. 1039-1041.

Tamiya et al., "Micro Glucose Sensors Using Electron Mediators Immobilized on a Polypyrrole-Modified Electrode," Sensors and Actuators, 1989, pp. 297-307, v.18.

Tsukagoshi et al., "Specific Complexation with Mono- and Disaccharides That Can Be Detected by Circular Dichroism," J. Org. Chem., 1991, pp. 4089-4091, vol. 56.

Urban et al., "Minaturized multi-enzyme biosensors integrated with pH sensors on flexible polymer carriers . . . ," Biosensors & Bioelectronics, 1992, pp. 733-739, vol. 7.

Urban et al., "Miniaturized thin-film biosensors using covalently immobilized glucose oxidase," Biosensors & Bioelectronics, 1991, pp. 555-562, vol. 6.

Velho et al., "In vivo calibration of a subcutaneous glucose sensor for determination of subcutaneous glucose kinetics," Diab. Nutr. Metab., 1988 pp. 227-233, v.3.

Yokoyama et al., "Integrated Biosensor for Glucose and Galactose," Analytica Chimica Acta., 1989, pp. 137-142, vol. 218.

Nishida et al., "Development of a ferrocene-mediated needle-type glucose sensor . . . ," Medical Process Through Technology, 1995, pp. 91-103, vol. 21.

Koudelka et al., "Planar Amperometric Enzyme-Based Glucose Microelectrode," Sensors and Actuators, 1989, pp. 157-165, vol. 18.

Yamasaki et al., "Direct measurement of whole blood glucose by a needle-type sensor," Clinica Chimica Acta., 1989, pp. 93-98, vol. 93.

Sternberg et al., "Study and Development of Multilayer Needle-type Enzyme-based Glucose Microsensors," Biosensors, 1988, pp. 27-40, vol. 4.

Shaw et al., "In vitro testing of a simply constructed, highly stable glucose sensor suitable for implantation . . . ," Biosensors & Bioelectronics, 1991, pp. 401-406, vol. 6.

Poitout et al., "A glucose monitoring system for on line estimation in man of blood glucose concentration using a miniaturized . . . ," Diabetologia, 1993, pp. 658-663, vol. 36.

Hashigushi et al., "Development of a Miniaturized Glucose Monitoring System by Combining a Needle-Type Glucose Sensor . . . ," Diabetes Care, 1994, pp. 387-389, v.17, n.5.

Jobst et al., "Thin-Film Microbiosensors for Glucose-Lactate Monitoring," Anal. Chem., 1996, p. 3173-3179, vol. 68.

Shults et al., "A Telemetry-Instrumentation System for Monitoring Multiple Subcutaneously Implanted Glucose Sensors," IEEE Trans. on Biomed. Eng., 1994, pp. 937-942, v41, n.10.

Wang et al., "Needle-Type Dual Microsensor for the Simultaneous Monitoring of Glucose and Insulin," Anal. Chem., 2001, pp. 844-847, vol. 73.

Moussey et al., "Performance of Subcutaneously Implanted Needle-Type Glucose Sensors Employing a Novel Trilayer Coating," Anal. Chem., 1993, 2072-77, vol. 65.

Bindra et al., "Design and In Vitro Studies of a Needle-Type Glucose Sensor for Subcutaneous Monitoring," Anal. Chem., 1991, pp. 1692-1696, vol. 63.

* cited by examiner

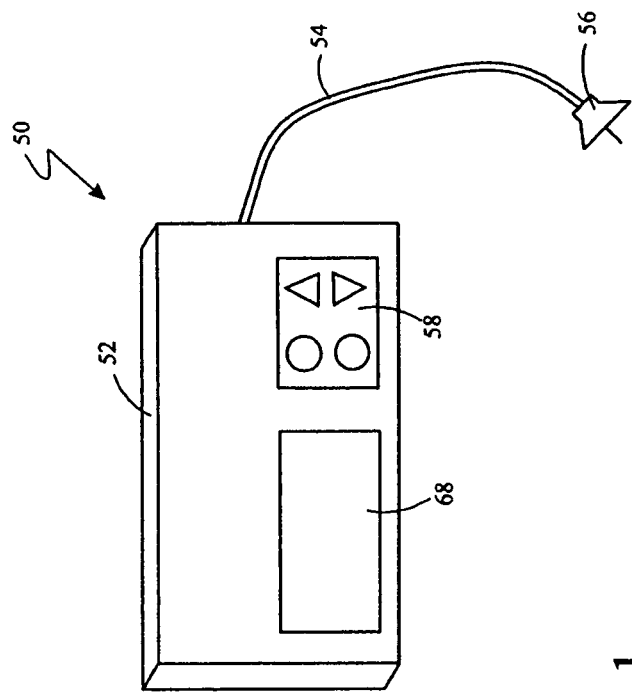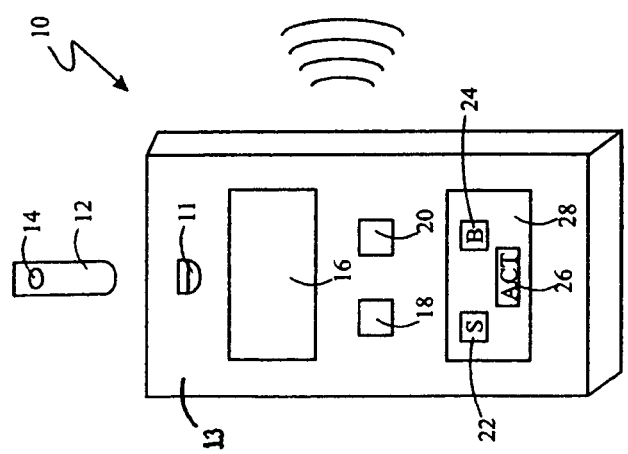
FIG. 1

SYSTEM FOR PROVIDING BLOOD GLUCOSE MEASUREMENTS TO AN INFUSION DEVICE

RELATED APPLICATIONS

This application is a continuation-in-part of U.S. patent application Ser. No. 10/624,389 filed Jul. 22, 2003 now abandoned, which claims priority from U.S. Provisional Application No. 60/398,199 filed Jul. 24, 2002 and 60/412,998 filed Sep. 23, 2002, and also claims priority from U.S. Provisional Application No. 60/478,697 filed Jun. 13, 2003, which are herein incorporated by reference.

FIELD OF THE INVENTION

This invention relates generally to infusion systems that are used for infusing a fluid into a user, and in particular, to apparatuses and methods for providing blood glucose measurements to an infusion device.

BACKGROUND OF THE INVENTION

Patients with Type I diabetes and some patients with Type 2 diabetes use insulin to control their blood glucose (BG) level. Typically, if a patient's BG level is too high, the patient can inject a "bolus" (dose) of insulin to lower his/her BG level from its present level to a desired target level. Furthermore, patients may inject a bolus of insulin in anticipation of ingesting carbohydrates, thus heading off a sharp rise in their BG level. Patients employ various calculations to determine the amount of insulin to inject. Bolus estimation software is available for calculating an insulin bolus. Patients may use these software programs on an electronic computing device, such as a computer, the Internet, a personal digital assistant (PDA), or an insulin delivery device. Insulin delivery devices include infusion pumps, injection pens, and IV meters. The best bolus estimation software takes into account the patient's present BG level. Presently, a patient must measure his/her blood glucose using a BG measurement device, such as a test strip meter ("meter"), a continuous glucose measurement system, a hospital hemacue, or an automated intermittent blood glucose measurement system. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device. Then the patient may visually read the BG measurement and physically enter the BG measurement into an electronic computing device to calculate a bolus estimate. Finally, once the bolus estimate is calculated, the patient must inject the insulin bolus or program an insulin delivery device to deliver the bolus into their body. Unfortunately, this process is cumbersome and is subject to transcribing errors—for example, the patient may not accurately enter the BG measurement that is displayed on the BG measurement device into the electronic computing device. Thus, if the BG measurement is not entered correctly, the bolus estimate is not accurate. Furthermore, once the bolus estimation is complete, the patient may not accurately enter the bolus amount into a programmable infusion device, or the patient may read the bolus amount incorrectly and inject the wrong amount of insulin.

SUMMARY OF THE INVENTION

In preferred embodiments of the present invention, an infusion system for infusing a fluid into a body of a user includes a characteristic determining device and an infusion device. The characteristic determining device includes a housing adapted to be carried by the user, a receptacle coupled to the housing for receiving and testing an analyte from the user to determine a concentration of the analyte in the user, a processor contained in the housing and coupled to the receptacle for processing the determined concentration of the analyte from the receptacle, and a communication system contained in the housing and coupled to the processor for transmitting a communication including data indicative of the determined concentration of the analyte in the user. In particular embodiments, the characteristic determining device may also include a lancing device coupled to the receptacle for obtaining the analyte from the user. In preferred embodiments, the infusion device includes a housing adapted to be carried by the user, a drive mechanism contained in the housing and operatively coupled with a reservoir containing the fluid for infusing the fluid into the body of the user, a communication system contained in the housing for receiving the communication including the data indicative of the determined concentration of the analyte in the user from the determining device, and a processor contained in the housing and coupled to the communication system for processing the data indicative of the determined concentration of the analyte in the user and controlling the infusion device. The infusion device further includes a bolus estimator used in conjunction with the processor for calculating an estimated amount of fluid to be infused into the body of the user based upon the received data indicative of the determined concentration of the analyte in the user and a target concentration of the analyte in the user, and an indicator to indicate when the estimated amount of fluid to be infused has been calculated. Additionally, the infusion device may include a user input device for inputting an estimate of a material to be ingested by the user, and the bolus estimator may include the capability to calculate the estimated amount of fluid to be infused into the body of the user based upon the inputted estimate of the material to be ingested by the user. The infusion device may also include a memory for storing the data indicative of the determined concentration of the analyte in the user received by the infusion device communication system from the determining device communication system.

In particular embodiments, the characteristic determining device automatically transmits the communication including the data indicative of the determined concentration of the analyte in the user to the infusion device. In other particular embodiments, the characteristic determining device further includes a user input device for inputting commands, and transmits the communication including the data indicative of the determined concentration of the analyte in the user to the infusion device in response to a command from the user input device. In additional embodiments, the characteristic determining device further includes an indicator to indicate a status of the communication including the data indicative of the determined concentration of the analyte in the user being transmitted from the determining device communication system to the infusion device communication system.

In some embodiments, the communication transmitted from the characteristic determining device to the infusion device further includes a time at which the concentration of the analyte in the user was determined. In additional embodiments, the processor of the characteristic determining device determines an amount of time that has elapsed since the concentration of the analyte in the user was determined, and the communication transmitted from the determining device to the infusion device further includes the elapsed amount of time. Further, the processor of the characteristic determining device may cause the communication system of the characteristic determining device not to transmit the communication including the data indicative of the determined concentration of the analyte in the user if the elapsed amount of time exceeds a predetermined amount of time. In other embodiments, the infusion device processor determines an amount of time that has elapsed since the data indicative of the determined concentration of the analyte in the user was received, and causes the bolus estimator not to calculate the estimated amount of fluid to be infused based upon the determined concentration of the analyte if the elapsed amount of time exceeds a predetermined amount of time. In still other embodiments, the processor of the infusion device determines an amount of time that has elapsed since the concentration of the analyte in the user was determined, and causes the bolus estimator not to calculate the estimated amount of fluid to be infused based upon the determined concentration of the analyte if the elapsed amount of time exceeds a predetermined amount of time.

In further embodiments, the determining device communication system is capable of being deactivated and reactivated. The characteristic determining device includes a user input device for inputting commands, and the communication system of the characteristic determining device is capable of being deactivated in response to a first command from the user input device and being reactivated in response to a second command from the user input device. Alternatively, the communication system of the characteristic determining device may be automatically reactivated after a predetermined amount of time has elapsed or at a predetermined time of day. Additionally, the characteristic determining device may include a memory for storing data indicative of the determined concentration of the analyte in the user that is determined when the determining device communication system is deactivated, and the determining device communication system may transmit a communication including the stored data to the infusion device communication system when the determining device communication system is reactivated.

In still other embodiments, the processor of the characteristic determining device has unique identification information, and the communication transmitted from the characteristic determining device to the infusion device further includes the unique identification information of the determining device processor such that the infusion device is capable of discerning whether the communication is intended for receipt by the infusion device. In yet other embodiments, the processor of the infusion device has unique identification information, and the communication transmitted from the characteristic determining device to the infusion device further includes the unique identification information of the infusion device processor such that the infusion device is capable of discerning whether the communication is intended for receipt by the infusion device.

In preferred embodiments, the processor of the infusion device uses power cycling whereby power is periodically supplied to the communication system of the infusion device until a communication is received from the characteristic determining device. When a communication is received from the characteristic determining device, the processor of the infusion device discontinues using power cycling whereby the power is continuously supplied to the infusion device communication system. The infusion device processor may then resume using power cycling upon completing the receipt of the communication including the data indicative of the determined concentration of the analyte in the user from the determining device communication system.

In particular embodiments, the infusion system further includes a connector for coupling the characteristic determining device to a computer and downloading data from the characteristic determining device to the computer. The communication system of the infusion device is further capable of transmitting a communication including infusion device data to be downloaded, and the communication system of the characteristic determining device is further capable of receiving the communication including the infusion device data to be downloaded from the infusion device. The received infusion device data is then downloaded from the characteristic determining device through the connector to the computer. Alternatively, the characteristic determining device may further include a memory for storing data, and the received infusion device data may be stored in the memory of the characteristic determining device for subsequent downloading through the connector to the computer.

In other particular embodiments, the characteristic determining device further includes a user input device for inputting remote control commands for controlling the infusion device. The communication system of the characteristic determining device further transmits a communication including the remote control commands, and the communication system of the infusion device further receives the communication including the remote control commands from the characteristic determining device. The processor of the infusion device then controls the infusion device in accordance with the received remote control commands.

In yet other particular embodiments, the infusion device further includes a user input device for inputting remote control commands for controlling the characteristic determining device. The communication system of the infusion device further transmits a communication including the remote control commands, and the communication system of the characteristic determining device further receives the communication including the remote control commands from the infusion device. The processor of the characteristic determining device then controls the characteristic determining device in accordance with the received remote control commands.

In additional embodiments, the characteristic determining device further includes a determining device clock, and the infusion device further includes an infusion device clock. The infusion device communication system further transmits a communication including a time of the infusion device clock, and the determining device communication system further receives the communication including the time of the infusion device clock from the infusion device communication system. The determining device clock is then set to the received time of the infusion device clock. Alternatively, the determining device communication system further transmits a communication including a time of the determining device clock, and the infusion device communication system further receives the communication including the time of the determining device clock from the determining device communication system. The infusion device clock is then set to the received time of the determining device clock.

In accordance with another embodiment of the present invention, an infusion device infuses a fluid into a body of a user and is capable of communicating with a characteristic determining device, which is adapted for determining a concentration of an analyte in the user. The infusion device includes a housing adapted to be carried by the user, a drive mechanism contained in the housing and operatively coupled with a reservoir containing the fluid for infusing the fluid into the body of the user, a communication system contained in the housing for receiving a communication including data indicative of the determined concentration of the analyte in the user from the characteristic determining device, and a processor contained in the housing and coupled to the communication system for processing the data indicative of the determined concentration of the analyte in the user and controlling the infusion device. The infusion device also includes a bolus estimator used in conjunction with the processor for calculating an estimated amount of fluid to be infused into the body of the user based upon the received data indicative of the determined concentration of the analyte in the user and a target concentration of the analyte in the user. The infusion device further includes an indicator to indicate when the estimated amount of fluid to be infused has been calculated.

In accordance with still another embodiment of the present invention, a characteristic determining device determines a concentration of an analyte in a body of a user and is capable of communicating with an infusion device, which is adapted for infusing a fluid into the body of the user and calculating an estimated amount of the fluid to be infused into the body of the user based upon the determined concentration of the analyte in the user and a target concentration of the analyte in the user. The characteristic determining device includes a housing adapted to be carried by the user, a receptacle coupled to the housing for receiving and testing an analyte from the user to determine the concentration of the analyte in the user, a processor contained in the housing and coupled to the receptacle for processing the determined concentration of the analyte from the receptacle, and a communication system contained in the housing and coupled to the processor for transmitting a communication including data indicative of the determined concentration of the analyte in the user to the infusion device.

According to yet another embodiment of the present invention, an infusion system includes a characteristic determining device and an infusion device, and a method for infusing a fluid into a body of a user is provided. The method includes the steps of: receiving and testing an analyte from the user to determine a concentration of the analyte in the user, transmitting with the characteristic determining device a communication including data indicative of the determined concentration of the analyte in the user, and receiving with the infusion device the communication including the data indicative of the determined concentration of the analyte in the user. The data indicative of the determined concentration of the analyte in the user received by the infusion device from the characteristic determining device may then be stored in a memory of the infusion device. The method further includes the steps of calculating an estimated amount of fluid to be infused into the body of the user based upon the received data indicative of the determined concentration of the analyte in the user and a target concentration of the analyte in the user, and indicating when the estimated amount of fluid to be infused has been calculated. Additionally, the method may include the step of inputting an estimate of a material to be ingested by the user, and the estimated amount of fluid to be infused into the body of the user is calculated further based upon the inputted estimate of the material to be ingested by the user.

In some embodiments, the communication including the data indicative of the determined concentration of the analyte in the user is automatically transmitted from the characteristic determining device to the infusion device. In other embodiments, the communication including the data indicative of the determined concentration of the analyte in the user is transmitted from the characteristic determining device to the infusion device in response to an inputted command. In still other embodiments, the system indicates a status of the communication including the data indicative of the determined concentration of the analyte in the user being transmitted from the characteristic determining device to the infusion device.

In particular embodiments, the communication including the data indicative of the determined concentration of the analyte in the user transmitted from the characteristic determining device to the infusion device further includes a time at which the concentration of the analyte in the user was determined. In other particular embodiments, the system also determines an amount of time that has elapsed since the concentration of the analyte in the user was determined. In yet other particular embodiments, the system determines an amount of time that has elapsed since the communication including the data indicative of the determined concentration of the analyte in the user was received by the infusion device.

In additional embodiments, the method further includes the steps of transmitting with the infusion device a communication including a clock time of the infusion device, receiving with the characteristic determining device the communication including the clock time of the infusion device, and setting a clock time of the characteristic determining device to the received clock time of the infusion device. Alternatively, the method may include the steps of transmitting with the characteristic determining device a communication including a clock time of the characteristic determining device, receiving with the infusion device the communication including the clock time of the characteristic determining device, and setting a clock time of the infusion device to the received clock time of the characteristic determining device.

In accordance with a further embodiment of the present invention, an infusion system for infusing a fluid into a body of a user includes a characteristic determining device and an infusion device. The characteristic determining device includes a determining device housing adapted to be carried by the user, a sensor coupled to the determining device housing for determining a concentration of an analyte in the user, a determining device processor contained in the determining device housing and coupled to the sensor for processing the determined concentration of the analyte from the sensor, and a determining device communication system contained in the determining device housing and coupled to the determining device processor for transmitting a communication including data indicative of the determined concentration of the analyte in the user. The infusion device includes an infusion device housing adapted to be carried by the user, a drive mechanism contained in the infusion device housing and operatively coupled with a reservoir containing the fluid for infusing the fluid into the body of the user, an infusion device communication system contained in the infusion device housing for receiving the communication including the data indicative of the determined concentration of the analyte in the user from the determining device communication system, and an infusion device processor contained in the infusion device housing and coupled to the infusion device communication system for processing the data indicative of the determined concentration of the analyte in the user and controlling the infusion device.

In particular embodiments, the determining device communication system automatically transmits the communication including the data indicative of the determined concentration of the analyte in the user to the infusion device communication system. In other particular embodiments, the characteristic determining device further includes a user input device for inputting commands, and the determining device communication system transmits the communication including the data indicative of the determined concentration of the analyte in the user to the infusion device communication system in response to a command from the user input device. In further particular embodiments, the characteristic determining device includes an indicator to indicate a status of the communication including the data indicative of the determined concentration of the analyte in the user being transmitted from the determining device communication system to the infusion device communication system.

In some embodiments, the infusion device further includes a bolus estimator used in conjunction with the infusion device processor for calculating an estimated amount of fluid to be infused into the body of the user based upon the received data indicative of the determined concentration of the analyte in the user and a target concentration of the analyte in the user. The infusion device also includes an infusion device indicator to indicate when the estimated amount of fluid to be infused has been calculated. In other embodiments, the infusion device further includes a memory for storing data, and the data indicative of the determined concentration of the analyte in the user received by the infusion device communication system from the determining device communication system is stored in the memory of the infusion device.

In additional embodiments, the determining device processor has unique identification information, and the communication transmitted from the determining device communication system to the infusion device communication system further includes the unique identification information of the determining device processor such that the infusion device is capable of discerning whether the communication is intended for receipt by the infusion device. In yet additional embodiments, the infusion device processor has unique identification information, and the communication transmitted from the determining device communication system to the infusion device communication system further includes the unique identification information of the infusion device processor such that the infusion device is capable of discerning whether the communication is intended for receipt by the infusion device.

In further embodiments, the determining device communication system is capable of being deactivated and reactivated. The characteristic determining device may also include a memory for storing data indicative of the determined concentration of the analyte in the user that is determined when the determining device communication system is deactivated. The determining device communication system then transmits a communication including the stored data to the infusion device communication system when the determining device communication system is reactivated.

In still further embodiments, the infusion device processor uses power cycling whereby power is periodically supplied to the infusion device communication system until a communication is received from the determining device communication system. The infusion device processor discontinues using power cycling whereby the power is continuously supplied to the infusion device communication system when the communication including the data indicative of the determined concentration of the analyte in the user is received from the determining device communication system. Further, the infusion device processor resumes using power cycling upon completing the receipt of the communication including the data indicative of the determined concentration of the analyte in the user from the determining device communication system.

In other embodiments, the infusion system further includes a connector for coupling the characteristic determining device to a computer and downloading data from the characteristic determining device to the computer. The infusion device communication system is further capable of transmitting a communication including infusion device data to be downloaded, and the determining device communication system is further capable of receiving the communication including the infusion device data to be downloaded from the infusion device communication system. The received infusion device data is then downloaded from the characteristic determining device through the connector to the computer. The download may be transparent to the user. The download may occur whenever the computer senses the presence of the infusion device or characteristic determining device, when the infusion device or characteristic determining device is placed in a cradle, and/or at certain, predetermined times. The download may be a partial download. In further embodiments, the computer and/or several devices are configured to share information with each other.

In yet other embodiments, the characteristic determining device further includes a determining device clock, and the infusion device further includes an infusion device clock. The infusion device communication system further transmits a communication including a time of the infusion device clock, and the determining device communication system further receives the communication including the time of the infusion device clock from the infusion device communication system. The determining device clock is then set to the received time of the infusion device clock. Alternatively, the determining device communication system further transmits a communication including a time of the determining device clock, and the infusion device communication system further receives the communication including the time of the determining device clock from the determining device communication system. The infusion device clock is then set to the received time of the determining device clock.

In yet further embodiments, the infusion system comprises an infusion device and a sensing device. The sensing device includes a sensor and a transmitter in communication with the infusion device. The sensing device may sense an analyte of a bodily fluid of the user. The sensing device may be calibrated using data from the infusion device and/or from a characteristic determining device. In further embodiments, the sensing device senses additional physiological characteristics. In still further embodiments, the system is set up to automatically call for assistance when analytes reach a certain level. The call may include a global positioning system (GPS) location.

BRIEF DESCRIPTION OF THE DRAWINGS

A detailed description of embodiments of the invention will be made with reference to the accompanying drawings, wherein like numerals designate corresponding parts in the several figures.

FIG. 1 is a perspective view of a blood glucose meter and an infusion pump in accordance with an embodiment of the present invention.

DETAILED DESCRIPTION OF THE PREFERRED EMBODIMENTS

Figure 2:
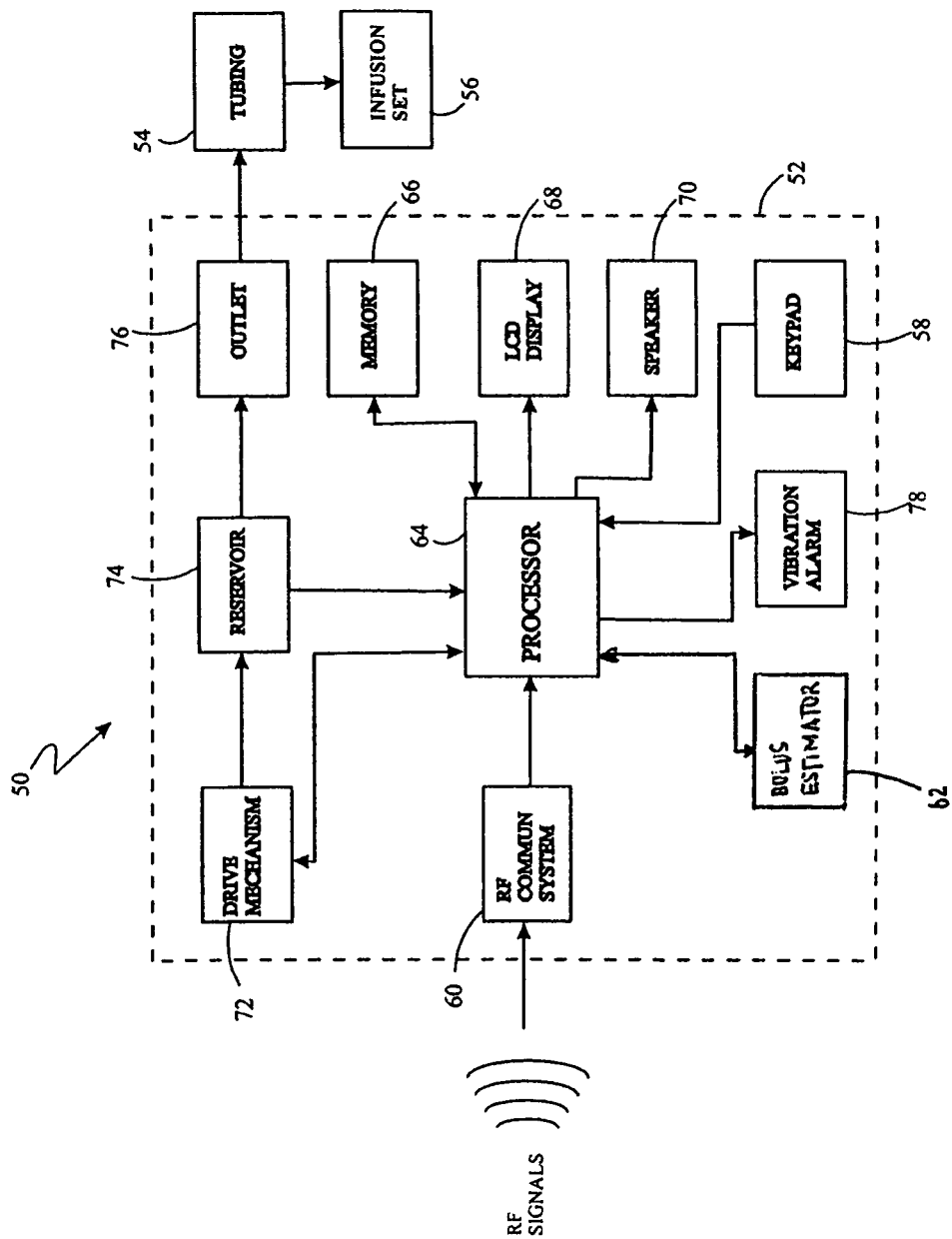
FIG. 2 is a simplified block diagram of an infusion pump in accordance with an embodiment of the present invention.

As shown in the drawings for purposes of illustration, the invention is embodied in a system for communicating blood glucose measurements from a blood glucose measurement device to an electronic computing device, which utilizes the blood glucose measurements to calculate a bolus estimate. In preferred embodiments, the blood glucose (BG) measurement device is a blood glucose (BG) test strip meter, and the electronic computing device is an insulin delivery device, preferably an external insulin infusion pump. The BG meter utilizes a test strip with a sample of the user's blood to measure the user's BG level, and then transmits the BG measurement to the infusion pump using a communication system that includes, for example, a radio frequency (RF) transmitter or transceiver. The infusion pump receives the BG measurement from the BG meter, and includes bolus estimation software to calculate a bolus estimate using the received BG measurement. The infusion pump may then deliver a bolus amount to the user based on the calculated bolus estimate. Transmission of the BG measurement from the BG meter to the infusion pump eliminates user transcription errors (i.e., the user may not accurately enter the BG measurement into the infusion pump) and simplifies the use of a bolus estimator. In particular embodiments, the BG meter may also function as a remote controller for the infusion pump, so the user can initiate a bolus delivery (without the bolus estimator) or stop a bolus delivery using buttons located on the BG meter. The BG meter may further function as a communications link for downloading data from the infusion pump to a computer or the like.

However, in alternative embodiments of the present invention, the BG measurement device may be a continuous glucose measurement system, a hospital hemacue, an automated intermittent blood glucose measurement system, and the like, and/or the BG measurement device may use other methods for measuring the user's BG level, such as a sensing device including a sensor in contact with a body fluid, an optical sensor, an enzymatic sensor, a fluorescent sensor, a blood sample placed in a receptacle, or the like.

In further alternative embodiments, the electronic computing device may be another type of insulin delivery device, such as an implantable insulin infusion pump or system that uses a combination of implantable and external components, an injection pen, an IV meter, and the like. In other alternative embodiments, the electronic computing device may be a computer, the Internet, a personal digital assistant (PDA), a portable telephone, a custom computing device, and the like. In still further alternative embodiments, the BG measurement device may use samples from body fluids other than blood, such as interstitial fluid, spinal fluid, saliva, urine, tears, sweat, or the like. In yet other alternative embodiments, other measurement devices may be utilized to determine the concentrations, levels, or quantities of other characteristics, analytes, or agents in the user, such as hormones, cholesterol, oxygen, pH, lactate, heart rate, respiratory rate, medication concentrations, viral loads (e.g., HIV), or the like. In still other alternative embodiments, other fluids may be delivered to the user, such as medication other than insulin (e.g., HIV drugs, drugs to treat pulmonary hypertension, iron chelation drugs, pain medications, and anti-cancer treatments), chemicals, enzymes, antigens, hormones, vitamins, or the like. Particular embodiments are directed towards the use in humans; however, in alternative embodiments, the infusion devices may be used in animals.

In addition to, or in lieu of, the BG measurement device such as the BG meter, the present invention may include a sensing device, which senses analyte values. In preferred embodiments, the analyte values are BG values. The sensing device preferably includes a sensor in contact with a bodily fluid of the user and a transmitter, wired and/or wireless. The BG sensor data are transmitted to the electronic computing device, for example an insulin delivery device, preferably an external insulin infusion pump. BG measurement values from the BG measurement device, such as the BG meter, are also sent to the electronic computing device. The sensor data is calibrated using the BG measurement values, and the calibrated sensor data and/or BG measurement values are shown on a display of the electronic computing device. In still further embodiments, the sensor is incorporated into the electronic computing device. The electronic computing device may transmit sensor data to the BG measurement device and/or the sensor data may be used in the electronic computing device. The sensor data is calibrated using BG measurement values from the BG meter, which may be transmitted to the electronic computing device and/or entered into the electronic computing device manually. The calibrated sensor data and/or BG measurement values may then be displayed on the display of the electronic computing device.

In preferred embodiments of the present invention, a blood glucose (BG) measurement device measures a user's BG level and then communicates the BG measurement to an electronic computing device, which utilizes the BG measurement to calculate a bolus estimate. In the embodiment illustrated in FIG. 1, the BG measurement device is a BG test strip meter 10, and the electronic computing device is an insulin delivery device, preferably an external insulin infusion pump 50.

Figure 4A:
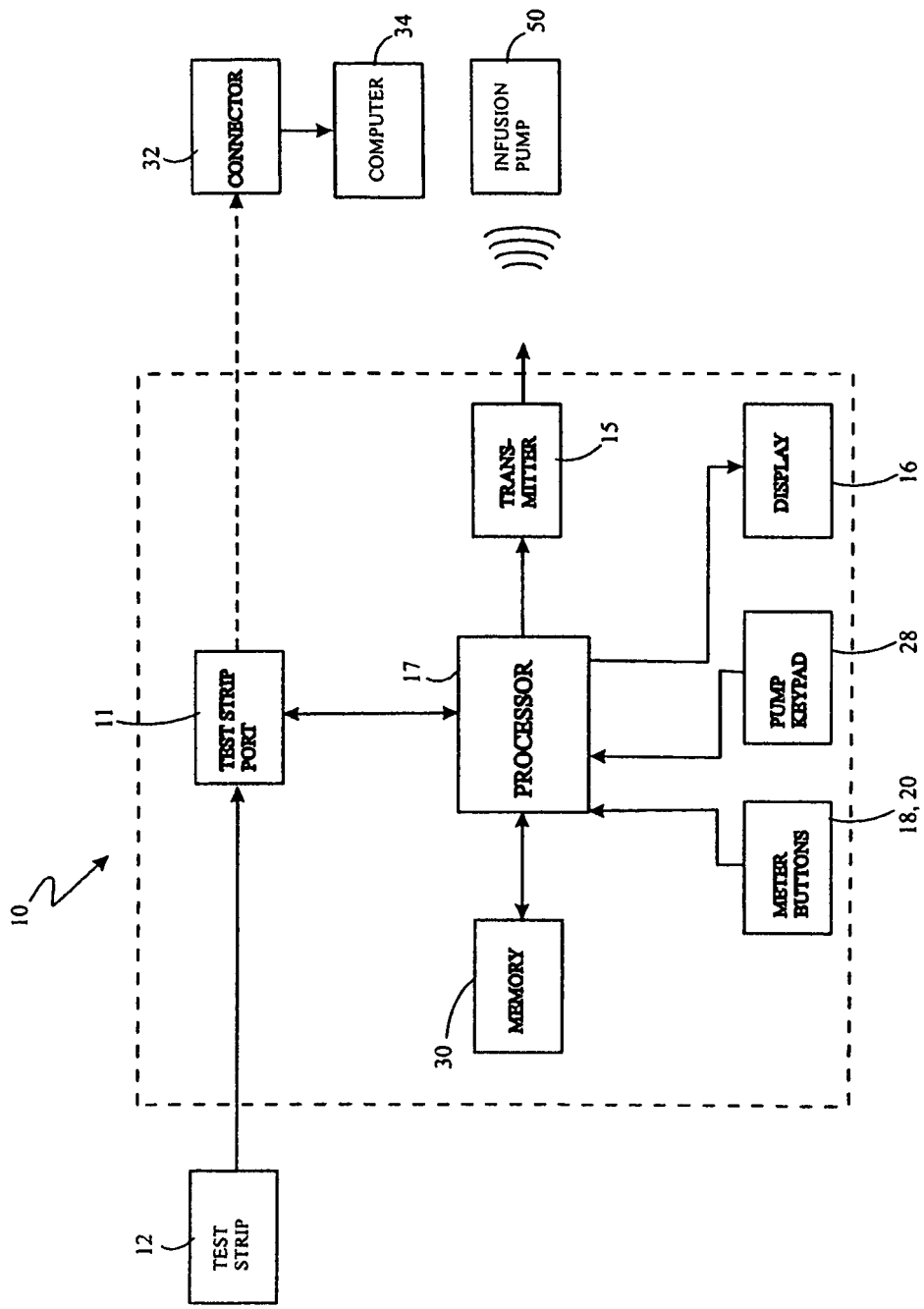
FIG. 4(a) is a simplified block diagram of a blood glucose meter in accordance with an embodiment of the present invention.

Referring to FIGS. 1 and 4(a), a housing 13 of the BG meter 10 preferably includes a test strip receptacle or port 11 for receiving and analyzing a test strip 12 or the like with a sample of the user's blood 14 on the test strip 12 to obtain a BG measurement. The BG meter 10 is adapted to be carried by the user, for example, in the hand, on the body, in a clothing pocket, attached to clothing (e.g., using a clip, strap, adhesive, or fastener), and the like. In particular embodiments, the user may utilize a separate lancing device (not shown) to obtain a blood sample, and then apply the sample onto the test strip 12. In other particular embodiments, the BG meter 10 may incorporate a lancing device (not shown) that obtains and automatically applies the blood sample onto the test strip 12.

In alternative embodiments, the BG measurement device may be a continuous glucose measurement system, a hospital hemacue, an automated intermittent blood glucose measurement system, and the like, and/or the BG measurement device may use other methods for measuring the user's BG level, such as a sensor in contact with a body fluid, an optical sensor, an enzymatic sensor, a fluorescent sensor, a blood sample placed in a receptacle, or the like. The BG measurement device may generally be of the type and/or include features disclosed in U.S. patent application Ser. No. 09/377,472 filed Aug. 19, 1999 and entitled "Telemetered Characteristic Monitor System and Method of Using the Same," Ser. No. 09/334,996 filed Jun. 17, 1999 and entitled "Characteristic Monitor with a Characteristic Meter and Method of Using the Same," Ser. No. 09/487,423 filed Jan. 20, 2000 and entitled "Handheld Personal Data Assistant (PDA) with a Medical Device and Method of Using the Same," and Ser. No. 09/935,827 filed Aug. 23, 2001 and entitled "Handheld Personal Data Assistant (PDA) with a Medical Device and Method of Using the Same," which are herein incorporated by reference. Such BG measurement devices may be adapted to be carried by the user, for example, in the hand, on the body, in a clothing pocket, attached to clothing (e.g., using a clip, strap, adhesive, or fastener), and the like. In further alternative embodiments, the BG measurement device may use samples from body fluids other than blood, such as interstitial fluid, spinal fluid, saliva, urine, tears, sweat, or the like. In yet other alternative embodiments, other characteristic determining or measuring devices may be utilized to determine or measure the concentrations, levels, or quantities of other characteristics, analytes, or agents in the user, such as hormones, cholesterol, oxygen, pH, lactate, heart rate, respiratory rate, medication concentrations, viral loads (e.g., HIV), or the like.

In particular embodiments, once the BG meter 10 obtains a BG measurement, the BG measurement is transmitted to the infusion pump 50 using a communication system, which includes a radio frequency (RF) transmitter 15, as will be described below. In other particular embodiments, the RF transmitter 15 may be replaced with an RF transceiver 19 (as shown in FIG. 4(b)) or 36 (as shown in FIG. 5), and the BG measurement may be transmitted to the infusion pump 50 using the RF transceiver 19 or 36.

The test strip port 11 and RF transmitter 15 are coupled to a processor 17 contained in the housing 13 of the BG meter 10. The processor 17 runs programs and controls the BG meter 10, and is also connected to a memory 30 for storing programs, history data, user defined information and parameters, and the like. The BG meter 10 also preferably includes a display 16 for providing the BG measurement and/or messages, such as status or error messages, to the user. In particular embodiments, the display 16 may include a backlight for reading the display 16 in the dark.

Figure 4B:
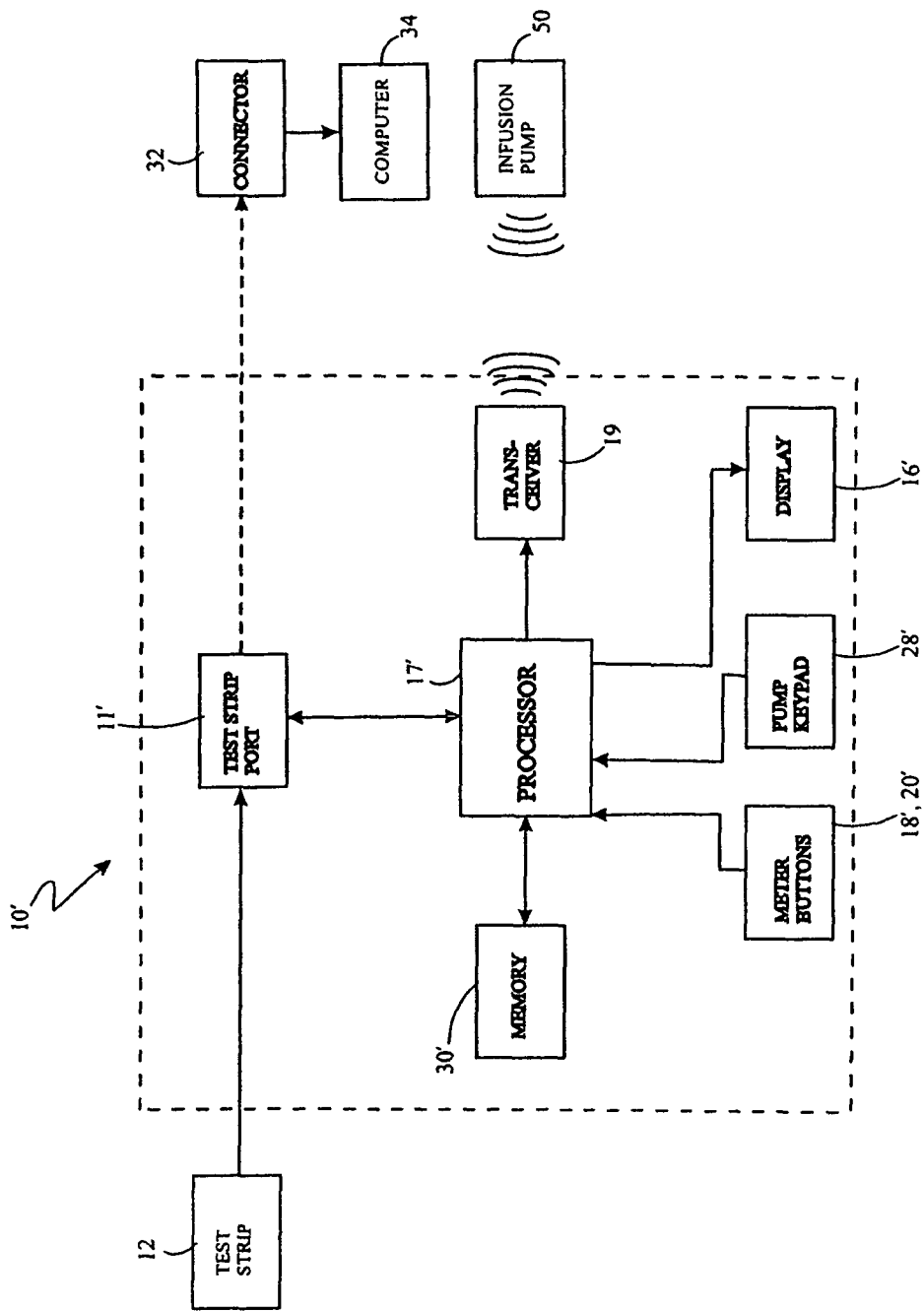
FIG. 4(b) is a simplified block diagram of a blood glucose meter in accordance with another embodiment of the present invention.
Figure 5:
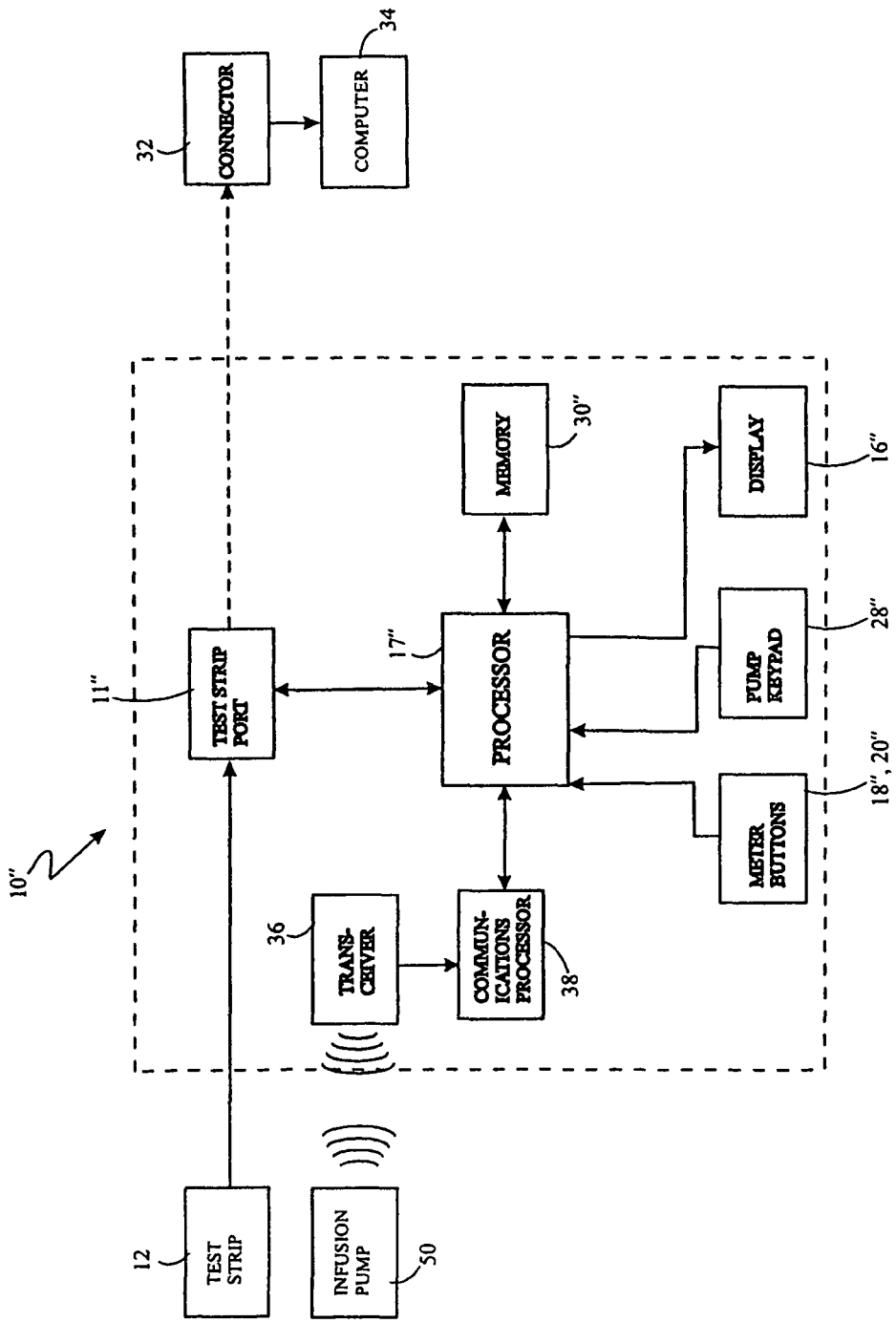
FIG. 5 is a simplified block diagram of a blood glucose meter in accordance with still another embodiment of the present invention.

In preferred embodiments, the BG meter 10 includes one or more buttons 18 and 20 for operation of the meter 10, such as turning on/off the meter 10, reviewing previous BG measurements, transmitting BG measurements to the infusion pump 50, turning off the transmitter 15 (or transceiver 19 (shown in FIG. 4(b)) or 36 (shown in FIG. 5)) in the BG meter 10 so that it does not send a BG measurement to the infusion pump 50, and the like. The BG meter 10 may further include a keypad 28 with one or more buttons 22, 24, and 26 that are preferably dedicated to remotely controlling the infusion pump 50, for example, via the RF transmitter 15 (or RF transceiver 19 (as shown in FIG. 4(b)) or 36 (as shown in FIG. 5)), as will be described below. The buttons 22, 24, and 26 may also be used to transmit BG measurements to the infusion pump 50. The buttons 22, 24, and 26 may be labeled 'S' for "suspend", 'B' for "bolus", and 'ACT' for "activate". In alternative embodiments, more or less buttons for operating the meter 10 and/or remotely controlling the infusion pump 50 may be included on the meter 10, and the buttons may be labeled other than as illustrated in FIG. 1. For example, the BG meter 10 may include an additional button for operating a lancing device (not shown) that is incorporated into the meter 10. In further alternative embodiments, the buttons 22, 24, and 26 may be omitted, and the buttons 18 and 20 may be used to remotely control the infusion pump 50. In other alternative embodiments, the buttons 18 and 20 may be omitted, and the buttons 22, 24, and 26 may be used to operate the BG meter 10, or alternatively, no buttons may be needed to operate the meter 10. For example, the meter 10 may include no buttons or other user interface or input device, and may be controlled using an external device, such as a remote programmer (not shown), the infusion pump 50, a PDA, or the like. In yet other alternative embodiments, one or more of the buttons 18, 20, 22, 24, and 26 may be omitted, and the user may utilize other input devices to interface with the BG meter 10, such as selecting a menu item, utilizing the display 16 as a touch screen, pressing multi-function keys, or the like.

In addition to transmitting the BG measurement to the infusion pump 50, the BG meter 10 also preferably stores the BG measurement in the memory 30 of the BG meter 10 for subsequent analysis and review. A history of alarms or error messages generated by the BG meter 10, as well as remote control commands sent to and/or information received from the infusion pump 50, may also be stored in the memory 30 of the BG meter 10. Further, the user may periodically cause the BG meter 10 to download the stored data through an interface (such as the RF transmitter 15 (or RF transceiver 19 (as shown in FIG. 4(b)) or 36 (as shown in FIG. 5)), a cable, a communication station, a cradle, or the like), to a computer 34 (e.g., desktop or portable computer, such as a laptop or personal data assistant (PDA)), or alternatively, over the Internet to a remote server for storage. The user or a caregiver (e.g., the user's parent, health care professional, educator) can evaluate the user's therapy by accessing the historical BG measurements and insulin delivery information downloaded from the pump 50, as will be described below. In other embodiments, the BG meter 10 may also obtain information from the computer 34 or remote server. It is therefore possible for information to be shared or transferred in either direction between the BG meter 10 and the computer 34 or remote server. In particular embodiments, a connector 32 may be inserted into the test strip port 11 to provide a wired connection to a USB, serial, or the like port of the computer 34, and data may be transferred through the connector 32 between the BG meter 10 and the computer 34. Alternatively, the computer 34 may be used in conjunction with a communications device (not shown) that allows the BG meter 10 or other devices, such as insulin pumps, to communicate with the computer 34. Examples of such communications devices include, without limitation, the ComLink™ available from Medtronic MiniMed, IR cradles, RF devices, or the like that can be used to send and/or receive signals. For instance, the ComLink™ or other RF device may be connected to the computer 34 via a wired connection, and the BG meter 10 may transfer data wirelessly to and from the computer 34 through the ComLink™ or other RF device using RF communication. In another instance, the IR cradle may be connected to the computer 34 via a wired or wireless connection, and the BG meter 10 may be placed in the IR cradle and transfer data to and from the computer 34 through the IR cradle.

The transfer of data between the BG meter 10 and the computer 34 or remote server may be transparent and performed without any user involvement, so that the user is not aware each time a data transfer is performed, except for any involvement the user may have had in setting up the transparent data transfer. Information may be transferred at the request of the user, at predetermined time intervals, or at any other interval. For example, the computer 34 may send out a communication signal (a ping) and listen for a response from the BG meter 10, which may respond to the ping through the interface (such as the RF transmitter 15 (or RF transceiver 19 (as shown in FIG. 4(b)) or 36 (as shown in FIG. 5)), a cable, a communication station, a cradle, or the like) to the computer 34. In response to the ping, the BG meter 10 may either transmit information to the computer 34 or download information from the computer 34. If the BG meter 10 is within the communication range of the computer 34, then the BG meter 10 will be able to download information from the computer 34 or transmit information to the computer 34. The BG meter 10 may also communicate with the computer 34 every time it is placed in a cradle (not shown) that is connected to the computer 34.

In further embodiments, the BG meter may be configured to download data (or transmit data) at a certain scheduled time. For example, the BG meter may communicate with the computer when the user is expected to be stationary and in a known location, such as when the user is sleeping. In such instance, a bedside monitor may be used to communicate between the BG meter and the computer. The bedside monitor may include a clock, communication capabilities, and a means for passing information to the computer. At a predetermined time, the bedside monitor will initiate a communication protocol attempting to communicate with the BG meter or other devices, such as an infusion pump, a BG sensor, other medical devices, and the like. If one or more devices respond to the bedside monitor communication, they will send information to the bedside monitor. The bedside monitor will pass the information from the one or more devices to a storage and/or display device such as a computer, a personal data assistant, or the like. The bedside monitor may also pass information from the storage and/or display device to another device, such as the infusion pump, BG meter, BG sensor, or other medical device. The bedside monitor may use one or more modes of communication with the storage and/or display device, such as wired communication, RF, infrared (IR) and the like. The bedside monitor may also be a computer or part of a computer.

In various embodiments, only the BG meter 10 may be used for downloading information to the computer 34. Thus, the BG meter 10 can communicate with and receive information for downloading to the computer 10 from other devices, such as the infusion pump 50 or a BG sensing device (as will be described below), through the communication system, which may include the RF transmitter 15 or RF transceiver 19 (as shown in FIG. 4(b)) or 36 (as shown in FIG. 5)). The BG meter keeps track of information received from the other devices, so each time the BG meter communicates with the other devices, the BG meter receives only new data from the other devices (i.e., data not yet received by the BG meter). In more particular embodiments, the BG meter receives new information from the other devices when the BG meter sends BG values to the other devices. In alternative embodiments, a device other than the BG meter may be used to gather data from the other devices, and to transfer data to the other devices and the computer or other storage device.

In further embodiments, two or more devices may share information between them. For example, a user may use two BG meters—one at home and one at work. If the two or more devices establish contact with each other, they share information that has been generated since the last time they communicated. For example, if the devices are two BG meters, they may send their respective BG measurements to each other so that each BG meter will have a complete record of BG measurements. In other embodiments, the two devices are not the same type of device. For example, one device may be a BG meter and the other device may be an insulin pump. The communication between the two or more devices may take place upon the user's instruction, whenever either device receives new data, or at other desired intervals.

Any of the communication described above with respect to the BG meter 10 is also possible to create with the insulin pump 50. For example, the insulin pump may download data to, and/or obtain information from, a computer or remote server, through an interface or communication system (as will be described below). It is possible for information to be shared or transferred in either direction between the insulin pump 50 and a computer or remote server. The transfer of data may be transparent, so that the user is not aware of the transfer while it is happening. Information may be downloaded at the request of the user, at predetermined time intervals, or at any other interval. The computer may send out a communication signal (a ping) and listen for a response from the insulin pump, which may respond to the ping through the interface or communication system described below. In response to the ping, the insulin pump may either transmit information to the computer or download information from the computer. If the insulin pump is within the communication range of the computer, then the insulin pump will be able to download information from the computer or transmit information to the computer. The insulin pump may also communicate with the computer every time it is placed in a cradle that is connected to the computer. Further, the insulin pump and the BG meter may be configured to each communicate with the computer at the same time or in turn.

Figure 6:
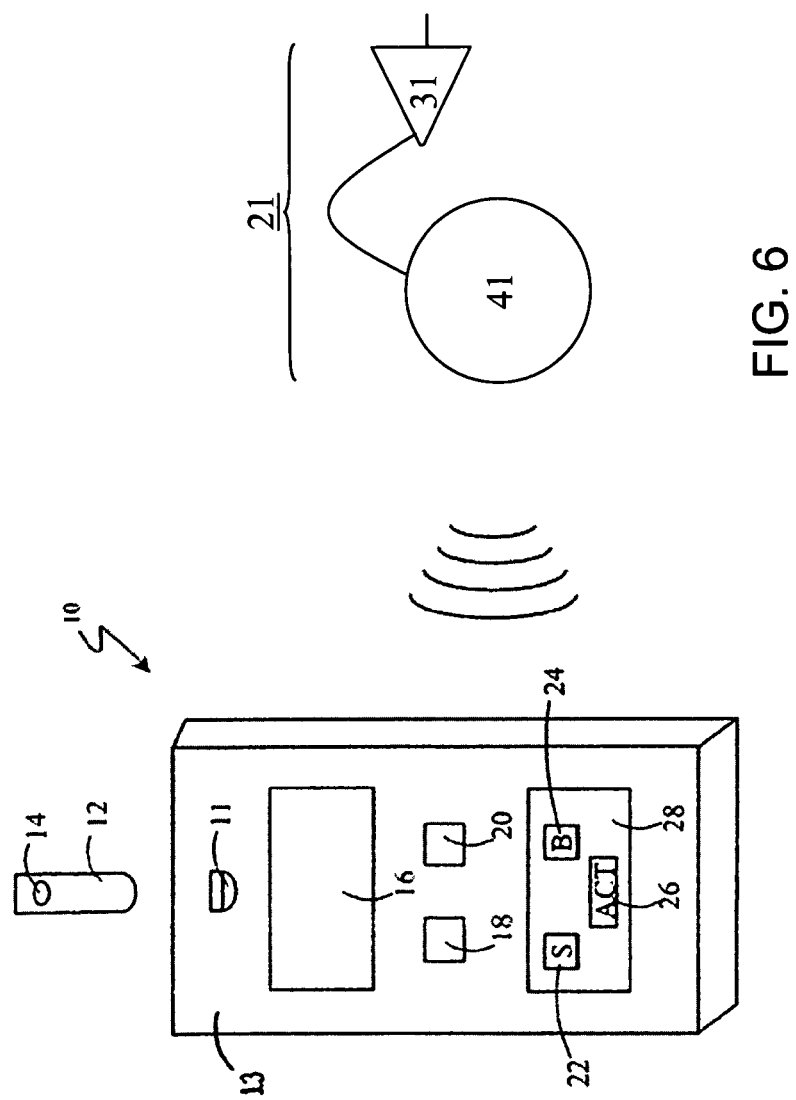
FIG. 6 is a perspective view of a sensing device in accordance with an embodiment of the present invention.

In further embodiments, the BG meter 10 is in communication with one or more sensing devices. For example, FIG. 6 shows an embodiment of a sensing device 21 that may be in communication with the BG meter 10. The sensing device 21 is preferably in contact with a bodily fluid (e.g., blood, interstitial fluid, or the like) of the user through sensor 31, and measures analyte levels of the user. For example, the sensor 31 may be adapted for insertion in subcutaneous or other tissue of the user, and may measure BG levels of the user. Alternatively, the sensing device 21 may measure physiological characteristics other than the user's BG levels, such as heart rate, respiratory rate, pH, oxygen, ketones, lactose, alcohol levels, and any other desired physiological characteristics. Sensing device 21 preferably also includes a transmitter 41, which is shown as being capable of wireless communication with the BG meter 10, but may be connected to the BG meter 10 through other means, such as a cable. In addition, transmitter 41 may be located on the same housing as sensor 31 or separated by a cable or other connection. The use of the term "transmitter" is not in any way meant to be limiting and may refer to any component that may be used to transfer the signal from the sensor to another device. Sensing devices that may be used include, but are not limited to, those described in U.S. Pat. No. 6,248,067 issued Jun. 19, 2001; U.S. Pat. No. 6,424,847 issued Jul. 23, 2002; U.S. Pat. No. 6,558,320 issued May 6, 2003; and U.S. Pat. No. 6,641,533 issued Nov. 4, 2003, and U.S. patent application Ser. No. 09/465,715 filed Dec. 17, 1999 and entitled "Telemetered Characteristic Monitor System and Method of Using the Same"; Ser. No. 10/180,732 filed Jun. 26, 2002 and entitled "Communication Station and Software for Interfacing with an Infusion Pump, Analyte Monitor, Analyte Meter, or the Like"; Ser. No. 10/034,139 filed Dec. 27, 2001 and entitled "System For Monitoring Physiological Characteristics"; Ser. No. 10/750,080 filed Dec. 31, 2003 and entitled "System For Monitoring Physiological Characteristics"; Ser. No. 10/429,385 filed May 5, 2003 and entitled "Handheld Personal Data Assistant (PDA) with a Medical Device and Method of Using the Same"; Ser. No. 10/141,375 filed May 8, 2002 and entitled "Real Time Self-Adjusting Calibration Algorithm for an Interstitial Glucose Concentration"; Ser. No. 10/036,093 filed Dec. 28, 2001 and entitled "Sensing Apparatus and Process"; and Ser. No. 10/750,978 filed Dec. 31, 2003 and entitled "Real Time Self-Adjusting Calibration Algorithm," and U.S. patent application Ser. No. 10/850,114 filed Jun. 3, 2004 and entitled "System for Monitoring Physiological Characteristics", which are herein incorporated by reference. In various embodiments, the sensing device 21 continuously measures analyte levels, such as BG levels, of the user. Alternatively, the sensing device 21 can measure the user's analyte levels intermittently and/or as desired by the user. For example, the sensing device 21 may measure the user's analyte levels approximately every minute, although measurements may be taken at shorter or longer time intervals (e.g., one second, ten seconds, thirty seconds, two minutes, five minutes, or the like). The BG meter 10 may be adapted to receive sensor values from the sensing device 21 continuously, intermittently, or at other desired times.

The BG meter 10 can display sensor values received from the sensing device 21, which are related to the user's analyte levels measured by the sensing device 21. For example, the BG meter 10 displays BG sensor values that are refreshed every one, five, ten, fifteen, or twenty minutes, or at other time intervals. Alternatively, the BG meter 10 may display BG sensor values in response to a request from the user utilizing the buttons 18 and 20 of the BG meter 10. The BG meter 10 may also provide the user with an alarm visually on the display 16, audibly via a speaker, and/or tactilely via a vibration alarm if the sensor values are either above or below certain predetermined levels, such as to indicate hypoglycemic or hyperglycemic conditions. The user may utilize the buttons 18 and 20 on the BG meter 10 to set hypoglycemic and/or hyperglycemic BG levels, or alternatively, these BG levels may be predefined for the BG meter 10 (e.g., hypoglycemic BG level of 70 mg/dl and hyperglycemic BG level of 200 mg/dl). In particular embodiments, the BG meter 10 calibrates the sensor values received from the sensing device 21. The calibration can be achieved by any known method, such as calibration based upon test strip readings taken by the BG meter 10. For example, whenever the user tests his BG by using a test strip, the BG meter 10 can compare this reading to the readings from the sensing device 21. If the sensor value is substantially different than the test strip value, the BG meter 10 will then adjust the sensor value to obtain a calibrated sensor value. Further discussion of methods of calibration can be found in U.S. Pat. No. 6,424,847, and U.S. patent application Ser. No. 09/465,715 filed Dec. 17, 1999 and entitled "Telemetered Characteristic Monitor System and Method of Using the Same"; Ser. No. 10/141,375, filed May 8, 2002 and entitled "Real Time Self-Adjusting Calibration Algorithm for an Interstitial Glucose Concentration"; and Ser. No. 10/750, 978 filed Dec. 31, 2003 and entitled "Real Time Self-Adjusting Calibration Algorithm," which are herein incorporated by reference. The BG meter 10 can take into account an estimated period of time that it takes a user to obtain a test strip blood sample and insert it into the BG meter 10. It is also possible to use other methods to calibrate the sensor values. For example, each sensor value can be calibrated based upon the history of sensor values. The sensing device 21 may include a processor (e.g., microprocessor, application specific integrated circuit or the like) for calibration of values, control of the device, and other processing. The sensing device 21 may further include a user interface (not shown) for input by the user, which may be wired to the transmitter 41 or may communicate with the transmitter 41 through wireless transmission. In further embodiments, the calibration can take place at the sensing device 21 instead of or in addition to at the BG meter 10. In this case, the BG meter 10 transmits a BG measurement to the sensing device 21 via a wired or wireless transmission, and the BG measurement is used to calibrate the BG sensor values measured by the sensing device 21. Alternatively, the BG measurement may be manually entered by the user into the sensing device 21 utilizing the user interface on the sensing device 21. The BG meter 10 then receives the calibrated sensor values from the sensing device 21, and may display the calibrated sensor values or other BG values related to the calibrated sensor values. In further embodiments, the sensing device 21 may include a display (not shown), which may be wired to the transmitter 41 or may communicate through wireless transmission. The display of the sensing device 21 may also show the raw sensor data and/or calibrated sensor data. The sensing device 21 may further provide the user with an alarm visually on the display, audibly via a speaker, and/or tactilely via a vibration alarm if the sensor values are either above or below certain predetermined levels, such as to indicate hypoglycemic or hyperglycemic conditions. The user may utilize the user interface of the sensing device 21 to set hypoglycemic and/or hyperglycemic BG levels, or alternatively, these BG levels may be predefined for the sensing device 21 (e.g., hypoglycemic BG level of 70 mg/dl and hyperglycemic BG level of 200 mg/dl). Additionally, if the BG meter 10 is used in connection with an infusion pump, the sensor data may be transmitted from the BG meter 10 and/or the sensing device 21 to the infusion pump.

In the embodiment illustrated in FIGS. 1 and 2, the electronic computing device is an insulin delivery device, preferably an external insulin infusion pump 50. The infusion pump 50 regulates the flow of fluid from the infusion pump 50, through a flexible tube 54, and into an infusion set 56 or the like that is adhered to the individual. Infusion sets 56 that may be used as a delivery device are described in, but not limited to, U.S. Pat. Nos. 4,723,947; 4,755,173; 5,176,662; 5,584, 813; and 6,056,718, which are herein incorporated by reference. The infusion pump 50 may be of the type described in U.S. Pat. Nos. 4,562,751; 4,685,903; 5,080,653; 5,097,122; 5,505,709; and 6,248,093; and disclosed in U.S. patent application Ser. No. 09/334,858, filed Jun. 17, 1999 and entitled "Infusion Pump With Remote Programming and Carbohydrate Calculator Capabilities," which are herein incorporated by reference. Such infusion pumps 50 may be adapted to be carried by the user, for example, in the hand, on the body, in a clothing pocket, attached to clothing (e.g., using a clip, strap, adhesive, or fastener), and the like. Alternatively, other infusion pumps 50 may be used for delivery of fluid through an infusion set 56 into an individual's body. In further alternative embodiments, devices other than infusion pumps 50 may be used for delivery of fluid into an individual's body, such as an implantable insulin infusion pump or system that uses a combination of implantable and external components, an injection pen, an IV meter, and the like. In other alternative embodiments, the electronic computing device may be a computer, the Internet, a personal digital assistant (PDA), a portable telephone, a custom computing device, and the like.

Figure 3A:
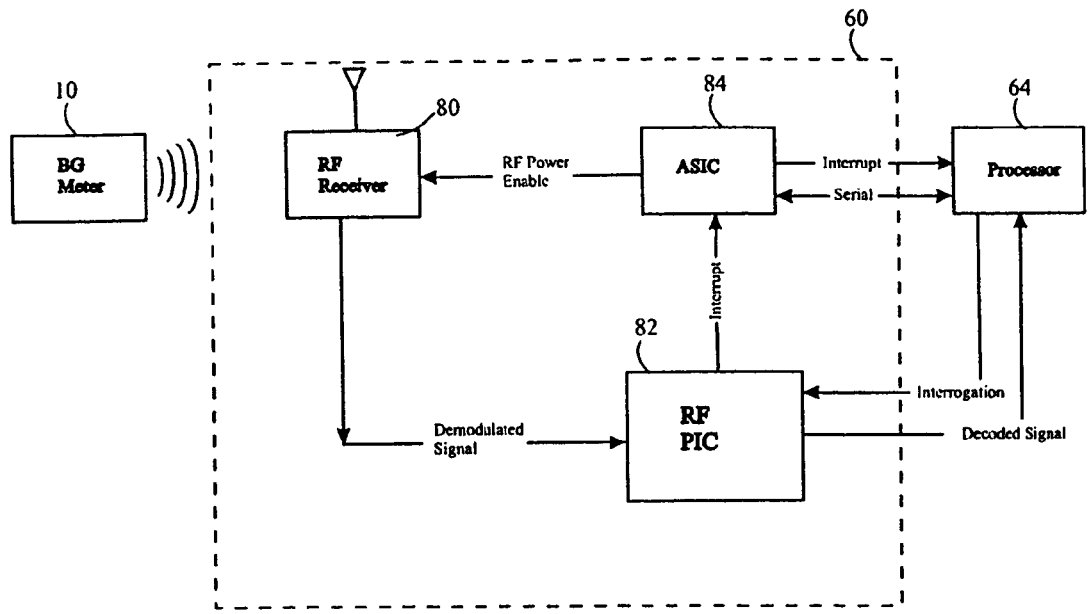
FIG. 3(a) is a block diagram of an RF communication system in the infusion pump in accordance with an embodiment of the present invention.
Figure 3B:
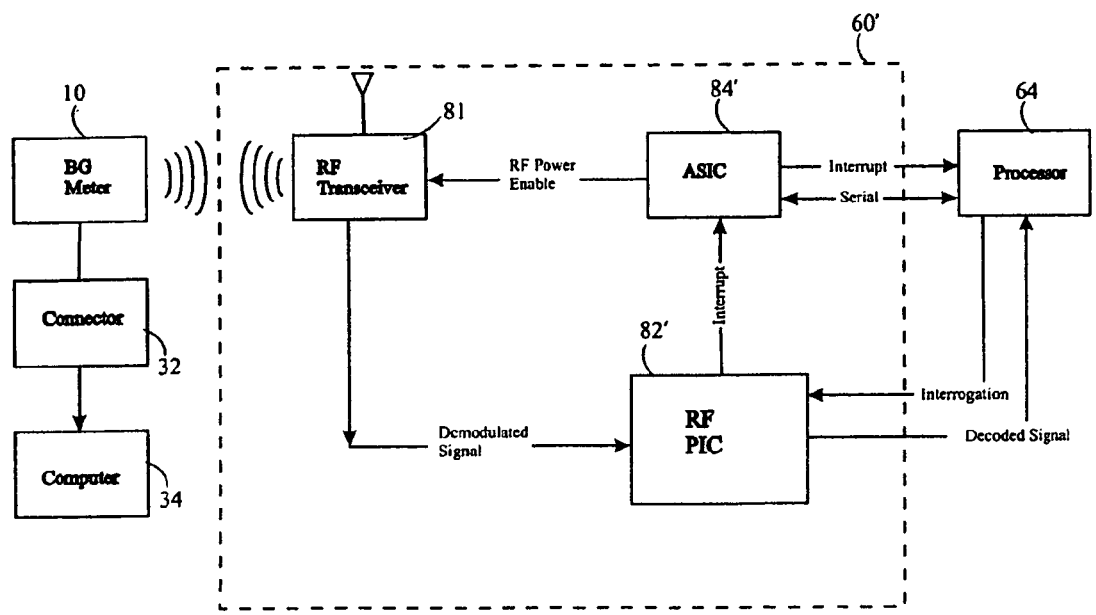
FIG. 3(b) is a block diagram of an RF communication system in the infusion pump in accordance with another embodiment of the present invention.

As illustrated in FIGS. 1 and 2, preferred embodiments of the infusion pump 50 include an RF communication system 60 and a bolus estimator 62. In particular embodiments, the RF communication system 60 includes an RF receiver 80, as shown in FIG. 3(a), which allows one-way communication from the BG meter 10 (or other external devices such as a remote programmer for the infusion pump 50) to the infusion pump 50. In other particular embodiments, the RF communication system 60' may include an RF transceiver 81, as shown in FIG. 3(b), which allows two-way communication between the BG meter 10 (or other external devices such as a remote programmer for the infusion pump 50) and the infusion pump 50.

The RF communication system 60 and bolus estimator 62 communicate with a processor 64 contained in a housing 52 of the infusion pump 50. The processor 64 is used to run programs and control the infusion pump 50, and is connected to an internal memory device 66 that stores programs, history data, user defined information and parameters. In preferred embodiments, the memory device 66 is a ROM and DRAM; however, in alternative embodiments, the memory device 66 may include other memory storage devices, such as RAM, EPROM, non-volatile memory, dynamic or semi-dynamic storage such as flash memory, energy efficient hard-drive, or the like. In the illustrated embodiment, the processor 64 is also coupled to a drive mechanism 72 that is connected to a fluid reservoir 74 containing fluid, which is delivered through an outlet 76 in the reservoir 74 and housing 52, and then into the user's body through the tubing 54 and the infusion set 56.

The infusion pump 50 is preferably programmed through a user input device such as a keypad 58 on the housing 52, or alternatively, by commands received from an RF programmer (not shown) through the RF communication system 60. The infusion pump 50 may also be programmed through the keypad 28 on the BG meter 10, for example, through the RF communication system 60, as will be described below. Feedback to the infusion pump 50 on status or programming changes are shown on a display 68, audibly through a speaker 70, and/or tactilely through a vibration alarm 78. The infusion pump 50 may also provide the user with an alarm either audibly via the speaker 70 and/or tactilely via the vibration alarm 78, such as a warning that is indicative of a low reservoir situation or low battery. Alarms may start out at a low level and escalate until acknowledged by the user. In alternative embodiments, the keypad 58 may include more or less keys or different key arrangements than those illustrated in FIG. 1. In further alternative embodiments, the keypad 58 may be omitted, and the display 68 may be used as a touch screen input device. In other alternative embodiments, the keypad 58, display 68, speaker 70, and/or vibration alarm 78 may be omitted, and all programming and data transfer may be handled through the RF communication system 60.

In particular embodiments, one-way communication is provided from the BG meter 10 to the infusion pump 50. The BG meter 10 includes the RF transmitter 15 (shown in FIG. 4(a)), and the infusion pump 50 includes an RF receiver 80 (shown in FIG. 3(a)). In other particular embodiments, two-way communication is provided between the BG meter 10 and the infusion pump 50. The RF transmitter 15 in the BG meter 10 is replaced with an RF transceiver 19 (shown in FIG. 4(b)) or 36 (shown in FIG. 5), and the RF receiver 80 in the infusion pump 50 is replaced with an RF transceiver 81 (shown in FIG. 3(b)).

The infusion pump 50 may provide several programming options, including the bolus estimator 62, as well as remote and on-device programming. The infusion pump 50 may also be configured through an interface, such as a cable or communication station, using a computer or the like. Additionally, the infusion pump 50 may allow the user to download information in the memory 66 through the interface to a computer or the like, or alternatively, over the Internet to a remote server, for storage. Further description of a communication station of this general type may be found in U.S. Pat. No. 5,376,070, which is herein incorporated by reference. The user or a caregiver (e.g., the user's parent, health care professional, educator) can evaluate the user's therapy by accessing the historical BG measurements downloaded from the BG meter 10 and insulin delivery information downloaded from the pump 50. In other embodiments, the infusion pump 50 may also obtain information from the computer or remote server. It is thus possible to transfer information in either direction between the infusion pump 50 and the computer or remote server.

Information may also be downloaded from, or received by, the infusion pump 50 through the RF communication system 60. Referring to FIG. 3(b), the RF communication system 60' may include the RF transceiver 81 for transmitting information to and receiving information from external devices. In particular embodiments, an external communication link (not shown) may be connected to a serial, USB, or the like port of a computer. Information may be transmitted from the RF transceiver 81 in the infusion pump 50 to an RF transceiver in the external communication link (not shown), which then downloads the information through a wired connection to the computer or the like. During the download process, the communication link may draw power from the computer through the serial, USB, or the like port. In other particular embodiments, the connector 32 may be inserted into the test strip port of the BG meter 10' to provide a wired connection to a USB, serial, or the like port of the computer 34, as shown in FIG. 4(b). Information may be transmitted from the RF transceiver 81 in the infusion pump 50 to the RF transceiver 19 in the BG meter 10', and may then be downloaded through the connector 32 to the computer 34. The BG meter 10' merely functions as a "pass through" connection between the infusion pump 50 and the computer 34. During the download process, power may be drawn from the power supply (not shown) for the BG meter 10' (e.g., battery or the like), or alternatively, from the USB, serial, or the like port of the computer 34. In still other particular embodiments, information may be transmitted from the RF transceiver 81 in the infusion pump 50 to the RF transceiver 36 in the BG meter 10", as shown in FIG. 5. The information may be transmitted from the infusion pump 50 to the BG meter 10" at a rate higher than can be handled by the meter processor 17". Accordingly, the BG meter 10" may include a communications microcontroller or processor 38 with a higher processing speed (e.g., 10 MHz) than the meter processor 17" with a lower processing speed (e.g., 1-4 MHz). The transmitted information is first processed by the communications processor 38, then processed by the meter processor 17", and finally downloaded through the connector 32 to the computer 34. Again, the BG meter 10' merely functions as a "pass through" connection between the infusion pump 50 and the computer 34. In alternative embodiments, information may be transmitted from the infusion pump 50 and stored in the memory 30' or 30" of the BG meter 10' or 10" for subsequent downloading from the BG meter 10' or 10" to the computer 34. In further alternative embodiments, information may be transmitted from the infusion pump 50 through the BG meter to the computer 34 using other modes of communication, such as infrared, optical, or the like. In other embodiments, information may be received by the infusion pump 50 from the computer.

Devices such as the infusion pump 50, BG meter 10, and sensing device 21 may learn each other's serial number and agree to listen to each other. Devices may also learn other identifying numbers or other characters or indicia, which may be unique, of each other (e.g., identification number, password, or the like). Communications among devices may include the unique identifying numbers or other identification information for one or more of the devices, and the devices utilize these unique identifying numbers or other identification information to discern between communications that are intended for the particular device and those that are not. The identifying numbers or other identification information may be chosen by a user or may be provided for the user (for example, a serial number could be added by the manufacturer or supplier). As an example, a user may place a pump into a mode so that it is ready to receive a signal from a meter containing the meter's serial number. When the signal is received, the user may tell the pump to accept and store the identifying number from the meter so that the pump can hear and accept other information from the meter in the future without requiring the user's approval, or the user can tell the pump to reject and not store the identifying number from the meter. If the pump stores the meter's identifying number, then future communications containing that identifying number will be accepted by the pump. The user may alternatively key in the identifying number through a user interface. Other devices may accept identifying numbers from still other devices. For example, in addition to the identifying number from the meter, the pump may also accept an identifying number from the sensing device. In alternative embodiments, a meter can send a signal to a pump without requiring that the user place the pump into a mode to receive a signal from the meter. When the pump detects the signal, the user can tell the pump to accept or reject the signal. The user can set the pump into a mode to not listen to unsolicited information (for example, signals from devices whose identifying numbers are not already in the pump). Additionally, in particular embodiments, devices will offer their identifying numbers to other devices without any interaction by the user.

Communication by devices between each other and with computer and other storage devices can be achieved through the use of any available communication architecture. Some examples of communication architecture include, without limitation, radio frequency based communication, such as high frequency radio wave communication like Bluetooth and such as wide bandwidth radio communication like spread spectrum, ultrasonic communication, and infrared communication.

Figure 7:
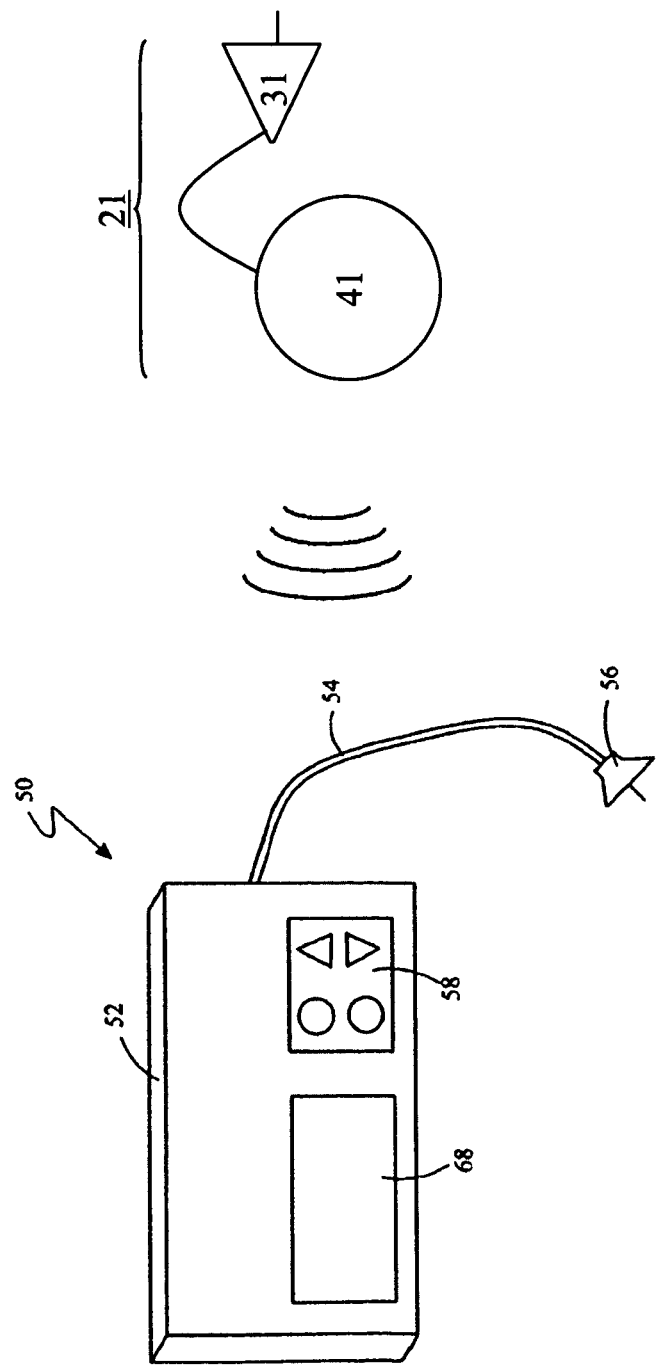
FIG. 7 is a perspective view of a sensing device in accordance with an embodiment of the present invention.

In further embodiments, as shown in FIG. 7, the infusion pump 50 may communicate with sensing device 21 instead of, or in addition to, the BG meter. The sensing device 21 may be connected to the infusion pump 50 by a wire, or communication between the infusion pump 50 and the sensing device 21 may be wireless. The infusion pump 50 may be adapted to receive sensor values including the user's measured analyte levels from the sensing device 21 continuously, intermittently, or at other desired times. The infusion pump 50 can then be used in conjunction with the BG meter 10, which transmits BG measurements to the infusion pump 50. These BG measurements may be used to calibrate the sensor values received from the sensing device 21. The raw or calibrated sensor values, as well as the BG measurements transmitted by the BG meter 10, can be displayed on the infusion pump display 68. For example, the infusion pump 50 may display BG sensor values that are refreshed every one, five, ten, fifteen, or twenty minutes, or at other time intervals. Alternatively, the infusion pump 50 may display BG sensor values in response to a request from the user utilizing the keypad 58 of the infusion pump 50. The infusion pump 50 may also provide the user with an alarm visually on the display 68, audibly via the speaker 70, and/or tactilely via the vibration alarm 78 if the sensor values are either above or below certain predetermined levels, such as to indicate hypoglycemic or hyperglycemic conditions. The user may utilize the keypad 58 of the infusion pump 50 to set hypoglycemic and/or hyperglycemic BG levels, or alternatively, these BG levels may be predefined for the infusion pump 50 (e.g., hypoglycemic BG level of 70 mg/dl and hyperglycemic BG level of 200 mg/dl). The infusion pump 50 may further display BG trends or graphs, provide the user with additional information, and/or include other features as described and disclosed in U.S. patent application Ser. No. 10/860,114 and entitled "System for Monitoring Physiological Characteristics", which is herein incorporated by reference. By enabling communication between the sensing device 21 and the infusion pump 50 in this way, the user is required to wear fewer or less bulky devices. For example, the sensing device 21 does not require a display because the sensor values can be transmitted to and shown on the infusion pump 50. Also, the sensing device 21 does not need to calibrate the sensor values prior to transmitting them to the infusion pump 50 because the sensor values can be calibrated by the infusion pump 50 utilizing BG measurements received from the BG meter 10.

In further embodiments, when a BG value is above or below certain predetermined levels, such as when the user is experiencing hypoglycemia or hyperglycemia, the system will automatically call a service for assistance, for example, the system may dial a 911 operator. Depending on which device communicates with the sensing device 21, it is possible that either the BG meter 10 or the infusion pump 50 (or the sensing device 21 itself) may call the service for assistance. Additionally, the call for assistance may include a global positioning service (GPS) location, when the device establishing the call includes a GPS locator. The sensing device 21 may also measure and display physiological characteristics in addition to the user's BG levels, such as heart rate, respiratory rate, pH, oxygen, ketones, lactose, alcohol levels, and any other desired physiological characteristics. These characteristics may be displayed on the device and also may be sent to the assistance service if they reach certain emergency levels.

In preferred embodiments, the infusion pump 50 communicates with various external devices, such as the BG meter 10, a remote programmer, and a communication station, using the RF communication system 60, which will be described below. The infusion pump 50 also provides a confirmation to the user upon receipt of a communication from another device (e.g., the BG meter 10). In particular embodiments, the infusion pump 50 provides one or more audible signals when it has received a communication. More than one audible signal may be used, and each audible signal indicates the type of communication that was received. For example, the infusion pump 50 may beep 4 times when it has received a communication to deliver 0.4 units of insulin in a bolus, provide a long low tone when it has received a communication to suspend insulin delivery, and/or sound off with a two-tone "door bell" sound when a new BG measurement has been communicated. In alternative embodiments, the infusion pump 50 may provide other forms of confirmation when a communication has been received, such as one or more vibrations via the vibration alarm 78, messages on the display 68, lights or flashing lights, or the like.

In preferred embodiments, once the BG meter 10 obtains a BG measurement, the BG meter 10 automatically transmits the BG measurement to the infusion pump 50. In particular embodiments, the BG meter 10 analyzes the blood sample 14 on the test strip 12 to calculate a BG measurement and then transmits the BG measurement to the infusion pump 50 without additional effort by the user. In alternative embodiments, the BG measurement is transmitted when the test strip 12 is removed from the BG meter 10. In other alternative embodiments, the BG meter 10 transmits the BG measurement in response to an action by the user. The BG meter 10 may also retransmit the BG measurement to the infusion pump 50 in response to a user action, such as pressing a button, selecting a menu item, or holding down a button on the BG meter 10, aligning the BG meter 10 and the infusion pump 50, or the like. In alternative embodiments, the BG meter 10 is notified by the infusion pump 50 to transmit or retransmit the BG measurement.

Once the infusion pump 50 receives the BG measurement, the infusion pump 50 may provide an alarm or warning to the user if the received BG measurement is above or below glycemic limits. The glycemic limits are preferably programmable, such as 120 mg/dl for hyperglycemia and 60 mg/dl for hypoglycemia. The user, a caregiver, a physician, a parent, a guardian, a child, or the like may program other limits into the infusion pump 50. In alternative embodiments, the glycemic limits are not programmable. In preferred embodiments, the infusion pump 50 will suspend insulin delivery if the received BG measurement is below the hypoglycemic limit. The infusion pump 50 may also notify the user to activate a bolus delivery if the received BG measurement is above the hyperglycemic limit. In alternative embodiments, the infusion pump 50 does not compare the received BG measurement to glycemic limits, and does not suspend insulin delivery in the event of hypoglycemia or notify the user to activate bolus delivery in the event of hyperglycemia.

In preferred embodiments, the infusion pump 50 also stores the received BG measurement in its memory 66. Further, the bolus estimator 62 in the infusion pump 50 may utilize the received BG measurement to calculate a bolus estimate, either automatically or in response to user input, such as through the keypad 58, a remote programmer, or the like. Once the bolus estimate is calculated and provided to the user, for example, on the display 68, the user may then approve the recommended estimate for delivery into the body, modify the recommended estimate for delivery into the body, or reject the recommended estimate. The bolus estimator 62 may generally be of the type and/or include features disclosed in U.S. patent application Ser. No. 09/334,858 filed Jun. 16, 1999, now issued U.S. Pat. No. 6,554,798 issued Apr. 29, 2003.

The BG meter 10 preferably informs the user of the status of the BG measurement calculation and/or transmission. If the infusion pump 50 is capable of only one-way communication, such notification is preferable because no confirmation is received from the infusion pump 50 indicating that the transmitted data has been received by the pump 50. The BG meter 10 may notify the user when a blood sample is being analyzed to obtain a BG measurement. The BG meter 10 may also notify the user when the BG measurement is being transmitted to the infusion pump 50. The BG meter 10 may further notify the user when the transmission of the BG measurement is complete. Once notified that the transmission of the BG measurement is complete, the user may access the bolus estimator 62 in the infusion pump 50 to view the BG measurement and calculate a bolus. In preferred embodiments, the BG meter 10 displays the status on the display 16, for example, as an alphanumeric message, a graphical icon, or the like. In alternative embodiments, the status is communicated to the user in other ways, such as using one or more light emitting diodes, one or more audible tones, a speaker, a piezo electric device, a vibrator or other tactile device, or the like. In further alternative embodiments, the BG meter 10 may not provide the status to the user. For example, if the BG measurement device provides continuous or automatic intermittent BG measurements, the user is not perpetually notified regarding the status of the calculations and/or transmissions.

In preferred embodiments, the BG meter 10 keeps track of the elapsed time between when a BG measurement is collected and when it is communicated to the infusion pump 50 for calculating a bolus estimate. A BG measurement is preferably used to calculate a bolus estimate only if the BG measurement is recent enough. The bolus estimation is at least partially dependent on the difference between the user's present BG level and a desired target BG level. Since a user's BG level varies over time, using an old BG measurement to calculate a bolus estimation might result in a bolus estimation that is inappropriate for the user. A BG measurement is expired (and is not used for bolus estimation) when it is too old to be considered representative of the user's present BG level. The BG meter 10 does not transmit a BG measurement to the infusion pump 50 for use in a bolus estimation calculation if the BG measurement is expired. The BG meter 10 may also indicate to the user that a new BG measurement is required because the BG measurement is expired or unavailable. In preferred embodiments, the BG measurement expires at 10 minutes. In alternative embodiments, the BG measurement may expire in an amount of time greater or less than 10 minutes, such as 5 or 7 minutes, 15 or 30 minutes, 1 hour, or the like. In further alternative embodiments, the time required for a BG measurement to expire may be set by the user, a caregiver, a physician, a parent, a guardian, a child, and the like. For example, a child's BG level may change more quickly than that of a heavy adult, so the BG meter 10 may be set so that BG measurements older than 5 minutes cannot be communicated to the infusion pump 50 for use in a bolus estimation. To continue the example, an adult might program the BG meter 10 so that BG measurements expire after 12 minutes. Furthermore, the time required for a BG measurement to expire may be set depending on the time of the user's most recent bolus dose of medication. A first period may be set if the user has taken a bolus within a specified duration of time, and a second period may be set if the user has not taken a bolus within the specified duration of time. For example, the time required for a BG measurement to expire may be set to 5 minutes if the user has taken a bolus within the past 2 hours, and to 15 minutes if the user has not taken a bolus within the past 2 hours.

In preferred embodiments, the infusion pump 50 does not use an expired BG measurement in a bolus estimation calculation. The infusion pump 50 preferably keeps track of the time between when a new BG measurement is received from the BG meter 10 and when the new BG measurement is used in a bolus estimation calculation. In particular embodiments, once the BG meter 10 obtains a BG measurement, the BG measurement is immediately transmitted to the infusion pump 50, either automatically or in response to a user action. Thus, when the infusion pump 50 receives a BG measurement, the pump 50 knows that the BG measurement was recent, and can calculate the approximate age of the BG measurement simply by determining the amount of time that has elapsed between when the BG measurement was received from the BG meter 10 and when the BG measurement is used in a bolus estimation calculation. In other particular embodiments, the infusion pump 50 is told the age of the BG measurements it receives. In other words, the elapsed time between when a BG measurement is collected and when it is communicated to the infusion pump 50 is transmitted along with each BG measurement. Then, the infusion pump 50 can calculate the age of the BG measurement by adding the age of BG measurement at the time it was transmitted to the time that has passed since the BG measurement was received. Since the infusion pump 50 knows the age of the BG measurement, the infusion pump 50 can eliminate BG measurements that are expired and/or prevent expired BG measurements from being used in a bolus estimation calculation. In particular embodiments, the infusion pump 50 will request a new BG measurement from the user when the user attempts to use a bolus estimator and the BG measurement is expired or unavailable.

In alternative embodiments, an estimate of the user's BG level is used for bolus estimation. In particular alternative embodiments, the user's BG level is estimated using the last BG measurement, the age of the BG measurement, the amount of insulin that has been delivered, the insulin action time, the number of carbohydrates consumed, the carbohydrate/insulin ratio, and the like. In further alternative embodiments, the estimate of the user's BG level will expire if not used soon enough. In still further alternative embodiments, the estimate of the user's BG level may only be calculated for a certain period after a BG measurement is collected. In other alternative embodiments, the length of time that a BG estimate may be calculated since a BG measurement was collected is determined by the amount of insulin that has been delivered, the amount of carbohydrates the user has ingested, the user's insulin sensitivity, and/or by the user's insulin action time. For example, estimates of BG levels may be calculated for a longer period if the user has not eaten lately and is using only basal insulin. If the user has eaten or taken a bolus of insulin, then the period of time that an estimate of the user's BG level might be calculated is shorter.

In preferred embodiments, the BG meter 10 communicates with the infusion pump 50 using RF communication. In alternative embodiments, other modes of communication may be used, such as infrared (IR), wired, ultrasonic, sonic, optical, and the like. The BG meter 10 transmits one or more BG measurements to the infusion pump 50. The BG meter 10 may also communicate one or more remote control commands to the infusion pump 50. The available commands preferably include a bolus amount of insulin, a command to begin insulin delivery, and a command to suspend insulin delivery. In alternative embodiments, more or less remote control commands may be provided between the BG meter 10 and the infusion pump 50. The RF transmitter 15 (or RF transceiver 19 (as shown in FIG. 4(b)) or 36 (as shown in FIG. 5)) in the BG meter 10 transmits the data (e.g., BG measurements or remote control commands) to the RF communication system 60 in the infusion pump 50. Additionally, the infusion pump 50 may communicate one or more user-defined parameters to the BG meter 10 (e.g., the time required for a BG measurement to expire). The RF transceiver 81 in the infusion pump 50 (shown in FIG. 3(b)) transmits such parameters to the RF transceiver 19 (as shown in FIG. 4(b)) or 36 (as shown in FIG. 5) in the BG meter 10' or 10".

In preferred embodiments, communication between the BG meter 10 and the infusion pump 50 contains unique identifying information about the BG meter 10 and/or infusion pump 50, such as the BG meter's 10 and/or infusion pump's 50 serial number, identification number, a password, a code, or the like. In particular embodiments, the unique identifying information about the BG meter 10 and/or infusion pump 50 included in the communication between the BG meter 10 and the infusion pump 50 is used by the respective devices (i.e., BG meter 10 and/or infusion pump 50) to discern between communications that are intended for the device and those that are not. In alternative embodiments, other codes may be included in communications between the BG meter 10 and the infusion pump 50 that are used by the respective devices to recognize which communications are intended for the device, such as an identification code for the device, a password, a bit sequence, a special frequency, timing between communications, or the like.

In preferred embodiments, the communication system in the BG meter 10 may be deactivated, preferably by the user. When the communication system is deactivated, the BG meter 10 will not attempt to communicate with other devices, including the infusion pump 50. For example, when a new BG measurement is available, the BG meter 10 will not communicate the BG measurement to another device, such as the infusion pump 50. In particular embodiments, the BG meter 10 includes an RF transmitter 15 (shown in FIG. 4(a)) (or RF transceiver 19 (shown in FIG. 4(b)) or 36 (shown in FIG. 5)) that can be deactivated and reactivated by the user. This is especially useful if the BG meter 10 transmits at frequencies that might disrupt an airplane during take-off. In alternative embodiments, other devices may be used to deactivate and reactivate the communication system in the BG meter 10, such as the infusion pump 50, other insulin delivery device, a computer, PDA, portable telephone, or the like. In preferred embodiments, the BG meter 10 may be programmed to reactivate its communication system after a certain duration. In particular embodiments, when the user deactivates the BG meter's communication system, the user is prompted to enter a duration for how long communication system is to be deactivated, and the communication system will automatically become active at the end of the duration. In alternative embodiments, the user may specify a time of day for the communication system to become active. In particular embodiments, all of the BG measurements that have been generated while the communication system was deactivated are transmitted to the infusion pump 50 when the communication system is reactivated. Other data may also be transmitted to the infusion pump 50, such as the BG meter's clock time when the BG measurement was generated (i.e., the timestamp for the BG measurement), the age of the BG measurement, and the like.

One-way communication is preferably used between the BG meter 10 and the infusion pump 50. The BG meter 10 includes a transmitter 15, and the infusion pump 50 includes a receiver 80. For example, the BG meter 10 transmits data (e.g., BG measurements or remote control commands), and the infusion pump 50 receives this data. The benefits of one-way communication (compared to two-way) include cheaper unit costs, less development time, and decreased battery power requirements. However, the drawback of one-way communication is that there is no confirmation that the BG meter 10 has transmitted the data to the infusion pump 50. Accordingly, in alternative embodiments, two-way communication may be used, and the BG meter 10 may include a transceiver 19 (as shown in FIG. 4(b)) or 36 (as shown in FIG. 5), and the infusion pump 50 may include a transceiver 81 (as shown in FIG. 3(b)).

In preferred embodiments, the infusion pump 50 uses power cycling to periodically supply power to its communication system. In alternative embodiments, the infusion pump 50 may not use power cycling, and instead, may continuously supply power to its communication system. The power cycle, which is one period that the communication system is off plus one period that the communication system is on, is preferably 8 seconds. In alternative embodiments, the power cycle may be shorter or longer than 8 seconds, such as 2 or 4 seconds, 12 or 15 seconds, or the like. Further, the period that the communication system is on during each power cycle is preferably 48 milliseconds (ms). In alternative embodiments, the period that the communication system is on during each power cycle may be greater or less than 48 ms, depending on the length of the message to be received, the communication frequency, the speed of the communication system electronics, and the like. In preferred embodiments, the BG meter 10 sends repeated signals to the infusion pump 50 for a period longer than the power cycle. The signal sent from the BG meter 10 to the infusion pump 50 preferably includes a command that is short enough to be captured during the on-time of the infusion pump's communication system. In particular embodiments, the command is short enough to be captured multiple times (i.e., two, three, or more times) during the on-time of the infusion pump's communication system.

In preferred embodiments, the time that the infusion pump's communication system must be on to capture the command from the BG meter 10 is short compared to the power cycle. In further embodiments, the command is short compared to a string of information. When the infusion pump 50 receives a command, the infusion pump 50 stops power cycling the communication system and turns the communication system on continuously. Alternatively, when the infusion pump 50 receives a command, the infusion pump 50 may continue to use power cycling unless the command indicates that the pump 50 should prepare to receive a string of information. Thus, short commands may be used to activate the infusion pump's communication system so that one or more longer strings of information may be received by the infusion pump 50.

In particular embodiments, the infusion pump 50 prepares to receive a string of information longer than a command. The string of information preferably includes a BG measurement. The string of information may further include an elapsed time since the BG measurement was taken. In alternative embodiments, the string of information may include a clock time. In further alternative embodiments, the BG meter 10 may transmit a clock time to the infusion pump 50 so that the infusion pump 50 can determine the difference between the BG meter's clock and the infusion pump's clock. In other alternative embodiments, the infusion pump 50 may use the BG meter's clock time to reset the infusion pump's clock time.

In preferred embodiments, the infusion pump 50 returns to power cycling the communication system after information has been received from the BG meter 10. In particular embodiments, the infusion pump 50 returns to power cycling after it receives a complete signal containing a BG measurement from the BG meter 10. In alternative embodiments, the infusion pump 50 returns to power cycling at a predetermined period after a signal from the BG meter 10 has stopped. In other alternative embodiments, the infusion pump 50 returns to power cycling at a predetermined period after receiving a signal from the BG meter 10.

As described above, the infusion pump 50 preferably communicates with various external devices, such as the BG meter 10, using the RF communication system 60. In particular embodiments, the RF communication system 60 includes an RF receiver 80, an RF microcontroller 82 (RF PIC), and an application specific integrated circuit 84 (ASIC), as shown in FIG. 3(*a*). In other particular embodiments, the RF receiver 80 may be replaced with an RF transceiver 81, as shown in FIG. 3(*b*). The RF PIC 82 may hold a 7-byte word, although in alternative embodiments, the RF PIC 82 may hold other lengths of data. The processor 64 communicates with the RF PIC 82 and the ASIC 84 using synchronous peripheral interfaces (SPI interfaces).

The RF receiver 80 receives and demodulates RF signals, extracts a data packet from the RF signal, and passes the data packet to the RF PIC 82. The RF PIC 82 accepts and decodes the data packet and checks for format. If the format of the data packet is valid, the RF PIC 82 sends an interrupt signal to the ASIC 84. When the ASIC 84 receives an interrupt signal from the RF PIC 82, the ASIC 84 sends an interrupt to the processor 64, triggering the processor 64 to notify the RF PIC 82 to pass the contents of its buffer to the processor 64. The processor 64 acquires the decoded data packet from the RF PIC 82 and evaluates the content, which may include a command or information to be stored. In response to some data packets, the processor 64 will send a command to the ASIC 84 to change the power conditions on the RF receiver 80. The processor 64 also processes the commands and information received from the BG meter 10, which may result in changing the bolus delivery on the infusion pump 50 or entering a BG measurement into the bolus estimator 62. One of the main tasks for the ASIC 84 is to enable and disable power on the RF receiver 80. Generally, the ASIC 84 cycles the power on the RF receiver 80 to save energy. If commanded by the processor 64, however, the ASIC 84 will enable the RF receiver 80 to be powered continuously.

Each RF transmission sent to the pump preferably includes an RF signal header followed by a command packet or an information packet. Since the pump's RF receiver 80 is likely to wake up in the middle of a command packet, the RF signal header at the start of each transmission helps the pump 50 to synchronize its data sampling and identify the first byte of a new command packet or information packet. The RF signal header is preferably the same for each transmission, and is transmitted at the start of each RF transmission. The RF signal header may include two parts: a preamble and a start signature. The preamble is a series of pulses used to train the pump's digital signal sampling, and allows the pump 50 to synchronize its pulse sampling with the pulse bits in the new transmission. The start signature notifies the pump RF PIC 82 when the first byte of a new packet is starting. In alternative embodiments, the RF signal header may include other data. In further alternative embodiments, the RF signal header may be omitted.

In particular embodiments, command packets are 7 bytes in length, and information packets are 71 bytes in length. In alternative embodiments, the command packets and/or information packets may be of different lengths. The last byte of every command or information packet is an 8-bit cyclic redundancy check (CRC) calculated on all the preceding bytes in the packet. Before a command or information packet is sent by the BG meter 10 to the infusion pump 50, it is encoded using a DC balanced encoding scheme, which translates 4 bits of data into 6 for transmission as follows:

| HEX | DC |
|---|---|
| 0 | 010101 |
| 1 | 110001 |
| 2 | 110010 |
| 3 | 100011 |
| 4 | 110100 |
| 5 | 100101 |
| 6 | 100110 |
| 7 | 010110 |
| 8 | 011010 |
| 9 | 011001 |
| A | 101010 |
| B | 001011 |
| C | 101100 |
| D | 001101 |
| E | 001110 |
| F | 011100 |

The result of the encoding is that the 7-byte command packets require transmission of 11 bytes and the 71-byte data packets require transmission of 107 bytes. Upon receipt of the 11-byte or 107-byte packets from the BG meter 10, the pump RF PIC 82 in the infusion pump 50 decodes the packet into the 7-byte command packet or the 71-byte information packet. The processor 64 then checks all packets for valid identification of the infusion pump 50 (e.g., identification or serial number) and CRC. If the identification of the infusion pump 50 is not valid, the packet is ignored. If the CRC of the first command packet is not valid, the command is ignored. Otherwise, the processor 64 sends a negative acknowledge (NAK) response to any packet with an invalid CRC.

Information packets (71 bytes) are much larger than command packets (7 bytes), and cannot be stored in the pump RF PIC 82, and thus, cannot be used to "wake up" the pump 50. Instead, a command packet must be sent to the pump 50 to turn on the pump's RF receiver 80 and prepare the pump 50 to receive an information packet. While power to the infusion pump's communication system (i.e. RF receiver 80) is being cycled, a command packet is repeatedly transmitted from the BG meter 10 to the infusion pump 50. If an RF signal (i.e. including the first command packet) is present when the pump's RF receiver 80 comes on, the pump 50 will attempt to store the contents of the signal in the pump RF PIC 82. The processor 64 will verify whether the content of the signal is a valid command packet. If the command packet is valid, then the pump 50 will stop power cycling and power the RF receiver 80 continuously. Only the first command packet must be transmitted repeatedly. After the RF receiver 80 is on full-time, other command packets can be sent to the pump 50 in quick succession (for example, as quickly as the user can press buttons on the BG meter 10 or other external device to send the new command packets). Additional command packets or an information packet may also be transmitted to the pump 50.

The pump 50 preferably recognizes two categories of command packets: remote control or bolus commands and BG measurement commands. Remote control or bolus commands directly control the pump's insulin bolus delivery. BG measurement commands may transmit a new BG measurement(s) from the BG meter 10 to the pump 50, or alternatively, prepare the pump 50 to receive an information packet containing a new BG measurement value as well as other related data (e.g., a clock time or timestamp of the BG measurement, the age of the BG measurement, or the like) from the BG meter 10.

The pump 50 may receive a bolus command from the BG meter 10 or a remote programmer associated with the pump 50. The bolus command preferably includes a type code indicating the type of device transmitting the message (e.g., the BG meter 10 or the remote programmer), unique identifying information about the pump 50 (e.g., serial number, identification number, password, or the like), a key code indicating which bolus command button has been pressed (e.g., button "S" 22, button "B" 24, or button "ACT" 26 on the BG meter 10), and a counter indicating the number of times that the button has been pressed. In alternative embodiments, the bolus command may include other information and/or omit some of this data. When the pump 50 receives the bolus command, the processor 64 filters the command to discern the counter value so that the pump 50 can respond to the number of times the user has pressed the button to adjust a bolus.

The pump 50 may also receive a BG measurement command from the BG meter 10. The BG measurement command is transmitted to the pump 50 to send a new BG measurement(s) from the BG meter 10 to the pump 50, or alternatively, to prepare the pump 50 to receive an information packet containing a new BG measurement as well as other related data (e.g., a clock time or timestamp of the BG measurement, the age of the BG measurement, or the like) from the BG meter 10. If the BG measurement command transmits a new BG measurement(s) from the BG meter 10 to the infusion pump 50, the command preferably includes a type code indicating the type of device transmitting the message (e.g., the BG meter 10), the BG measurement value(s), and unique identifying information about the meter 10 and/or pump 50 (e.g., serial number, identification number, password, or the like). If the BG measurement command is transmitted to prepare the pump 50 to receive an information packet containing a BG measurement and other related data from the BG meter 10, the command preferably includes a type code indicating the type of device transmitting the message (e.g., the BG meter 10), unique identifying information about the meter 10 and/or pump 50 (e.g., serial number, identification number, password, or the like), and a key code indicating that a new BG measurement is about to be transmitted. In alternative embodiments, the BG measurement command may include other information and/or omit some of this data.

In response to communications from the BG meter 10, the pump 50 typically sends an acknowledge (ACK) response. However, in particular embodiments, the BG meter 10 does not include an RF receiver, and the pump 50 does not include an RF transmitter, and thus, the pump 50 does not send an ACK response if the type code in the command (e.g., bolus or BG measurement command) indicates that the device transmitting the message is the BG meter 10. In alternative embodiments, both the BG meter 10 and the pump 50 may include an RF transmitter and receiver (i.e. transceiver 19 (shown in FIG. 4(*b*)) or 36 (shown in FIG. 5) in the BG meter 10' or 10", and transceiver 81 (shown in FIG. 3(*b*)) in the infusion pump 50), and thus, the pump 50 may send an ACK response to the BG meter 10. Additionally, the pump 50 may send its clock time to the BG meter 10, and the BG meter 10 may use the pump's clock time to reset the BG meter's clock time if the devices' clock times do not correspond with one another. Further, if the meter 10 does not receive an ACK response from the pump 50, the meter 10 may attempt to retransmit the communication to the pump 50, either immediately or at a later time.

When the pump 50 receives a command packet from the BG meter 10, the processor 64 will send a data packet through the ASIC 84, commanding the RF receiver 80 to remain on full-time for a specified number of minutes, to receive other command packets or an information packet. The RF receiver 80 may return to power cycling after the information packet has been received, a certain period of time after receiving a BG measurement command (in the event that the anticipated information packet does not arrive), a certain period of time after receiving a bolus command, or after-the battery in the pump 50 has been removed and replaced.

The pump RF PIC 82 remains in receive mode unless it has received a command to send from the processor 64, in which case it shall switch to transmit mode until the transmission is complete. Once the data has been transmitted, the pump RF PIC 82 automatically switches back to receive mode.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion device for infusing a fluid into a body of a user, wherein the infusion device is capable of receiving a communication from a sensing device adapted for determining a concentration of a first analyte in the user, and is capable of receiving a communication from an external hand-held characteristic determining device adapted for determining a concentration of a second analyte in the user, the infusion device comprising:

a housing adapted to be carried by a user;

a drive mechanism contained in the housing and operatively coupled with a reservoir containing a fluid for infusing the fluid into the body of the user;

a receiver contained in the housing for receiving the communication from the sensing device and the communication from the external hand-held characteristic determining device, the communication from the sensing device including sensor values indicative of the determined concentration of the first analyte in the user, and the communication from the external hand-held characteristic determining device including the determined concentration of the second analyte in the user;

a processor contained in the housing and coupled to the receiver for processing the sensor values received from the sensing device and the determined concentration of the second analyte in the user received from the external hand-held characteristic determining device, and for controlling the infusion device; and an indicator coupled to the processor to indicate the received sensor values and the received concentration of the second analyte in the user.

2. The infusion device according to claim 1, wherein the characteristic determining device is a blood glucose meter.

3. The infusion device according to claim 1, wherein the receiver receives uncalibrated sensor values from the sensing device, and the processor is further adapted to calibrate the received sensor values.

4. The infusion device according to claim 3, wherein the processor is further adapted to calibrate the sensor values based upon the received concentration of the second analyte in the user.

5. The infusion device according to claim 3, wherein the indicator is adapted to display the calibrated sensor values.

6. The infusion device according to claim 5, wherein the indicator is adapted to display the calibrated sensor values in response to input from the user.

7. The infusion device according to claim 1, wherein the receiver receives the communication from the sensing device using wireless communication.

8. The infusion device according to claim 1, wherein the concentration of the first analyte in the user determined by the sensing device is a blood glucose level of the user.

9. The infusion device according to claim 1, wherein the receiver receives the communication from the characteristic determining device using wireless communication.

10. The infusion device according to claim 1, wherein the concentration of the second analyte in the user determined by the characteristic determining device is a blood glucose level of the user.

11. The infusion device according to claim 1, wherein the indicator is adapted to provide at least one of a visual indication, an audible indication, or a tactile indication, to indicate when the sensor values are below or above predetermined levels.

12. The infusion device according to claim 1, further comprising a bolus estimator used in conjunction with the processor for estimating an amount of the fluid to be infused into the body of the user, and wherein the indicator indicates the estimated amount of the fluid to be infused.

13. The infusion device according to claim 1, wherein the infusion device is adapted to automatically contact an emergency response system when the sensor values are below or above predetermined levels.

14. The infusion device according to claim 1, wherein the communication received from the characteristic determining device further includes unique identification information of the characteristic determining device such that the infusion device is capable of deciding whether to accept the communication from the characteristic determining device.

15. The infusion device according to claim 1, wherein the processor has unique identification information, and the communication received from the characteristic determining device further includes the unique identification information of the processor of the infusion device such that the infusion device is capable of deciding whether to accept the communication from the characteristic determining device.

16. The infusion device according to claim 1, wherein the communication received from the sensing device further includes unique identification information of the sensing device such that the infusion device is capable of deciding whether to accept the communication from the sensing device.

17. The infusion device according to claim 1, wherein the processor has unique identification information, and the communication received from the sensing device further includes the unique identification information of the processor of the infusion device such that the infusion device is capable of deciding whether to accept the communication from the sensing device.

18. The infusion device according to claim 1, further comprising a memory for storing data including the sensor values received from the sensing device and the determined concentration of the second analyte received from the characteristic determining device.

19. The infusion device according to claim 18, wherein the data stored in the memory of the infusion device is downloaded from the infusion device to a computer.

20. The infusion device according to claim 19, further comprising a transmitter for transmitting the data to be downloaded from the infusion device to the computer.

21. The infusion device according to claim 20, wherein the transmitter is further adapted to transmit the data to be downloaded from the infusion device to the computer automatically at predetermined times.

22. The infusion device according to claim 20, wherein the receiver is further adapted to receive a signal from the computer, and the transmitter is further adapted to transmit the data to be downloaded from the infusion device to the computer automatically in response to the signal from the computer.

23. The infusion device according to claim 18, further comprising a transmitter for transmitting the data stored in the memory of the infusion device to the characteristic determining device for subsequent downloading to a computer.

24. The infusion device according to claim 1, wherein the infusion device is an insulin infusion pump.

25. The infusion device according to claim 1, wherein the receiver uses one of radio frequency, infrared, Bluetooth, and spread spectrum communication.

* * * * *